United States Patent [19]
Balkovec et al.

[11] Patent Number: 5,541,160
[45] Date of Patent: Jul. 30, 1996

[54] ANTIFUNGAL AND ANTI-PNEUMOCYSTIS COMPOUNDS, COMPOSITIONS CONTAINING SUCH COMPOUNDS, AND METHODS OF USE

[75] Inventors: James M. Balkovec, North Plainfield; Frances A. Bouffard, Scotch Plains; Regina M. Black, Cranford, all of N.J.

[73] Assignee: Merck & Co., Inc., Rahway, N.J.

[21] Appl. No.: 222,157

[22] Filed: Apr. 4, 1994

[51] Int. Cl.$^6$ ........................................ C12P 21/04
[52] U.S. Cl. ............................. 514/11; 530/317
[58] Field of Search ........................ 530/317; 514/11

*Primary Examiner*—Sharon Gibson
*Assistant Examiner*—Catherine S. Kilby Scalzo
*Attorney, Agent, or Firm*—Elliott Korsen; Mark R. Daniel

[57] ABSTRACT

Compounds represented by the formula I (SEQ ID NO. 1) are disclosed:

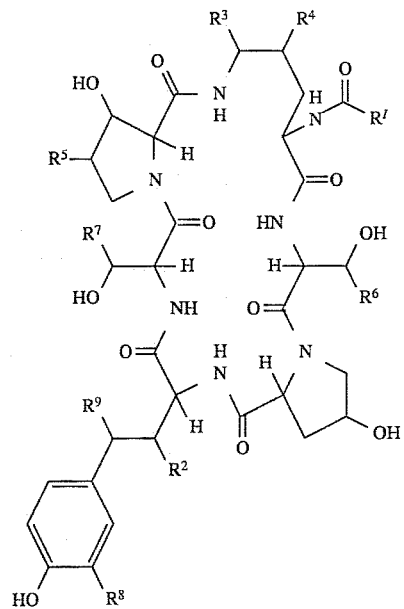

as well as pharmaceutically acceptable salts and hydrates thereof.

$R^I$ represents $C_9$ to $C_{19}$ alkyl, $C_9$ to $C_{19}$ alkenyl, an aryl group which includes phenyl, biphenyl, naphthyl and terphenyl or a $C_1$ to $C_{12}$ alkyl, alkylamino, dialkylamino or alkoxyaryl group.

$R^1$, $R^2$ and $R^4$ independently represent H or —OH.

$R^3$ represents H, —OH, —O(CH$_2$)$_n$NR$^V$R$^{VI}$, where $R^V$ and $R^{VI}$ independently represent H or $C_{1-4}$ alkyl, or —O(CH$_2$)$_n$NR$^V$R$^{VI}$R$^{VII+}$Y$^-$, wherein $R^V$ and $R^{VI}$ are as defined above, $R^{VII}$ represents H or $C_{1-4}$ alkyl, n is an integer of from 2–6 inclusive, and Y represents a counterion.

$R^5$ represents H, —CH$_3$ or —OH;

$R^6$ represents H or —CH$_3$;

$R^7$ represents H, —CH$_3$, —CH$_2$C(=O)NH$_2$, —(CH$_2$)$_2$NR$^V$R$^{VI}$ or —(CH$_2$)$_2$NR$^V$R$^{VI}$R$^{VII+}$Y$^-$ with n, $R^V$, $R^{VI}$ $R^{VII}$ and Y as defined above;

and $R^8$ represents —Cl, —Br, —I, —NO$_2$, —N$_3$, —(CH$_2$)$_{0-4}$NH$_2$, —(CH$_2$)$_{0-4}$NH(C$_{1-4}$ alkyl), —(CH$_2$)$_{0-4}$N(C$_{1-4}$ alkyl)$_2$, —(CH$_2$)$_{0-3}$CH(=NOH), —NHC(=O)(CH$_2$)$_{1-6}$NH$_2$ or —NHC(=O)(CH$_2$)$_{1-6}$NHC(=NH)(CH$_2$)$_{0-3}$H.

Pharmaceutical compositions and methods of use are also disclosed.

12 Claims, No Drawings

ANTIFUNGAL AND ANTI-PNEUMOCYSTIS COMPOUNDS, COMPOSITIONS CONTAINING SUCH COMPOUNDS, AND METHODS OF USE

BACKGROUND OF THE INVENTION

The present invention relates to antifungal and anti-Pneumocystis compounds with a substituent group at the 3' position of the homotyrosine peptide.

There presently exists a need for new antifungal and anti-Pneumocystis compounds due to an increase in the number of isolates which are resistant to conventional agents. Also, conventional agents show somewhat high levels of toxicity, which limits the usefulness of these agents. Lastly, the incidence of *Pneumocystis carinii* pneumonia is increasing, particularly in view of the high incidence of immunocompromised patients, e.g., suffering with AIDS.

SUMMARY OF THE INVENTION

Compounds represented by the formula I (SEQ ID NO. 1) are disclosed:

(SEQ ID NO. 1)     I as well as pharmaceutically acceptable salts and hydrates thereof.

$R^I$ represents $C_9$ to $C_{19}$ alkyl, $C_9$ to $C_{19}$ alkenyl, an aryl group which is selected from the group consisting of phenyl, biphenyl, naphthyl and terphenyl, or a $C_1$ to $C_{12}$ alkyl, alkylamino, dialkylamino or alkoxyaryl group.

$R^9$, $R^2$ and $R^4$ independently represent H or —OH.

$R^3$ represents H, —OH, —O(CH$_2$)$_n$NR$^V$R$^{VI}$, where $R^V$ and $R^{VI}$ independently represent H or $C_{1-4}$ alkyl, or —O(CH$_2$)$_n$NR$^V$R$^{VI}$R$^{VII+}$Y$^-$, wherein $R^V$ and $R^{VI}$ are as defined above.

$R^{VII}$ represents H or $C_{1-4}$ alkyl, n is an integer of from 2–6 inclusive, and Y represents a counterion.

$R^5$ represents H, —CH$_3$ or —OH;

$R^6$ represents H or —CH$_3$;

$R^7$ represents H, —CH$_3$, —CH$_2$C(=O)NH$_2$, —(CH$_2$)$_2$NR$^V$R$^{VI}$ or —(CH$_2$)$_2$NR$^V$R$^{VI}$R$^{VII+}$Y$^-$ with $R^V$, $R^{VI}$ $R^{VII}$ and Y as defined above;

and $R^8$ represents —Cl, —Br, —I, —NO$_2$, —N$_3$, —(CH$_2$)$_{0-4}$NR$^V$R$^{VI}$ with $R^V$ and $R^{VI}$ as previously defined, —(CH$_2$)$_{0-3}$CH(=NOH), —NHC(=O)(CH$_2$)$_{1-6}$NH$_2$ or —NHC(=O)(CH$_2$)$_{1-6}$NHC(=NH)(CH$_2$)$_{0-3}$H.

Pharmaceutical compositions am also included, which are comprised of a compound represented by formula I in combination with a pharmaceutically acceptable carrier.

A method of treating a fungal infection is also included, which is comprised of administering to a mammalian patient in need of such treatment a compound represented by formula I in an amount effective to treat the fungal infection.

A method of treating a *Pneumocystis carinii* infection is also included, which is comprised of administering to a mammalian patient in need of such treatment a compound represented by formula I in an amount effective to treat the *Pneumocystis carinii* infection.

A method of preventing a *Pneumocystis carinii* infection in an immunocompromised mammalian patient in need of such treatment is also included, which is comprised of administering to said patient an effective amount of a compound represented by formula I to prevent an occurrence of Pneumocystis infection.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 30 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to three substituent groups at any available point of attachment. When the alkyl group is said to be substituted with an alkyl group, this is used interchangeably with "branched alkyl group". When the alkyl group is substituted with a cycloalkyl group, the cycloalkyl group may be at any available point of attachment. The alkyl portion of "alkoxy" is also defined as above.

Cycloalkyl is a specie of alkyl containing from 3 to 15 carbon atoms, without alternating or resonating double bonds between carbon atoms. It may contain from 1 to 4 rings which are fused. The preferred cycloalkyl groups are cyclopentyl and cyclohexyl.

Aryl refers to aromatic tings e.g., phenyl, substituted phenyl and the like, as well as ting systems which are fused, e.g., naphthyl, phenanthrenyl and the like. Aryl groups may also contain one or more aryl groups singly bonded to each other. Aryl groups thus contain at least one ting having at least 6 atoms, with up to five such tings being present, containing up to 30 carbon atoms therein, with alternating (resonating) double bonds between adjacent carbon atoms. The preferred aryl groups are phenyl, biphenyl, naphthyl and terphenyl. When specified as such, aryl groups may likewise be substituted. Preferred substituted aryls include phenyl and naphthyl substituted with one or two such groups.

The term "halogen" refers to F, Cl, Br or I.

The term "heteroatom" means O, S or N, selected on an independent basis.

Aralkyl is a specie of substituted alkyl, containing up to three aryl groups substituted on a straight, branched or cycloalkyl group. The most preferred aralkyl group is benzyl (—CH$_2$C$_6$H$_5$).

Alkoxy refers to $C_1$–$C_4$ alkyl-O-, with the alkyl group optionally substituted.

The term "alkoxyaryl" thus refers to a $C_{1-12}$ alkyl-O- group, except where it is specified that the alkyl portion thereof is a different number of carbon atoms, e.g., $C_{9-20}$ alkyl. The alkoxy portion thereof is substituted on an aryl group, e.g., a phenyl ting, at any available point of attachment. Likewise, the substituent groups "alkylamino" and "dialkylamino" refer to substituent groups having one or two $C_{1-12}$ alkyl groups attached to a nitrogen atom, which is in turn substituted onto the aryl group which is selected from phenyl, biphenyl, naphthyl and terphenyl. When the aryl group is substituted with an alkyl radical, said alkyl radical is a $C_{1-12}$ group.

The term "echinocandin B nucleus" (SEQ ID NO. 2) refers to the structure:

(SEQ ID NO. 2)

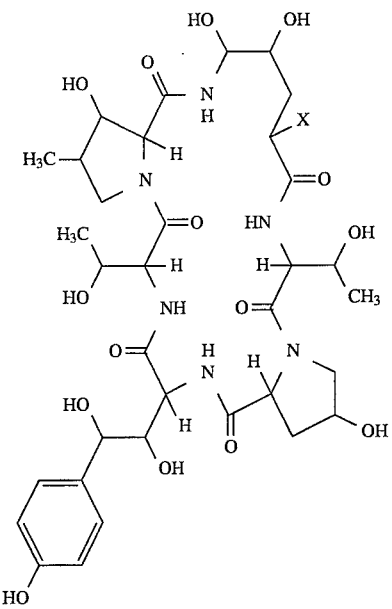

where X represents $NH_2$. In echinocandin B, X represents

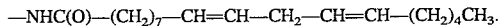

$-NHC(O)-(CH_2)_7-CH=CH-CH_2-CH=CH-(CH_2)_4CH_3$.

This lipophilic side chain can be removed enzymatically or through fermentative means. The nucleus typically is missing the side chain referred to above, and this is replaced with an alternate side chain in accordance with the chemical synthesis described herein.

When an alkyl, cycloalkyl or aryl group is termed "substituted", this means that from one to three substituent groups is present, at any available point of attachment. Substituent groups include the following: $C_{1-6}$ alkyl; halogen, as defined above; hydroxyl; amino; $C_{1-6}$ alkylamino; $C_{1-6}$ dialkylamino or $C_{1-6}$ alkoxy.

Where a particular substituent group is shown with a bond attached, e.g., when $R^9$ is equal to $-OCH_2CH_2NH_2$ the bond is shown drawn to the substituent group for purposes of identifying the point of attachment, and is not to be taken as an indication with the generic structure that a double bond is intended. Double bonds are plainly shown, such as in the imino group (=NH) attached to a carbon atom via a double bond when $R^8$ represents

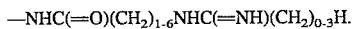

$-NHC(=O)(CH_2)_{1-6}NHC(=NH)(CH_2)_{0-3}H$.

A subset of compounds which are addressed herein is represented by formula I-a which (SEQ ID NO. 3) has the following formula:

(SEQ ID NO. 3)      I-a

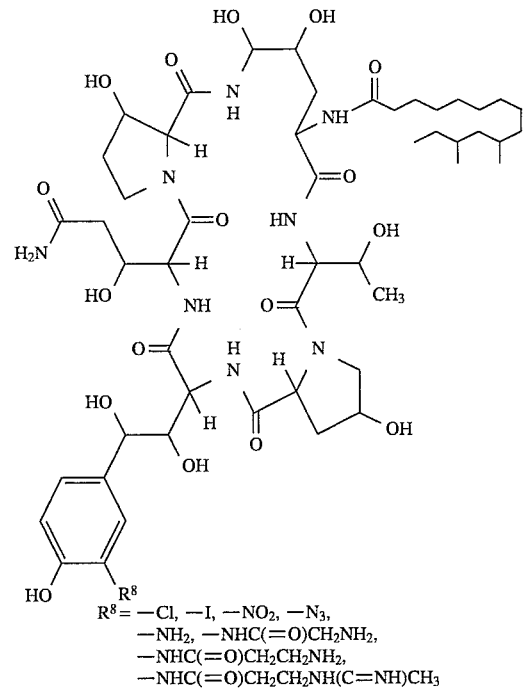

$R^8 = -Cl, -I, -NO_2, -N_3,$
$-NH_2, -NHC(=O)CH_2NH_2,$
$-NHC(=O)CH_2CH_2NH_2,$
$-NHC(=O)CH_2CH_2NH(C=NH)CH_3$

It is noted that the peptide at position six of the cyclic hexapeptide is a 3-hydroxyproline residue and the peptide at position one is a 4,5-dihydroxyornithine residue.

Another subset of compounds which fall within the present invention is represented by the formula I-b.

(SEQ ID NO. 4)      I-b

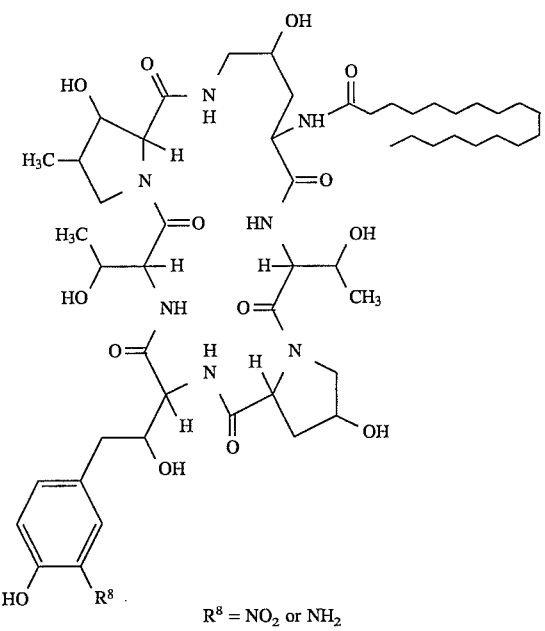

$R^8 = NO_2$ or $NH_2$

These compounds are characterized as including a threonine at position five, a 3-hydroxy-4-methyl proline residue at position six, and a 4-hydroxy ornithine at position one.

Another subset of compounds of the present invention is represented by formula 1-c set forth below.

(SEQ ID NO. 5)                                                          I-c

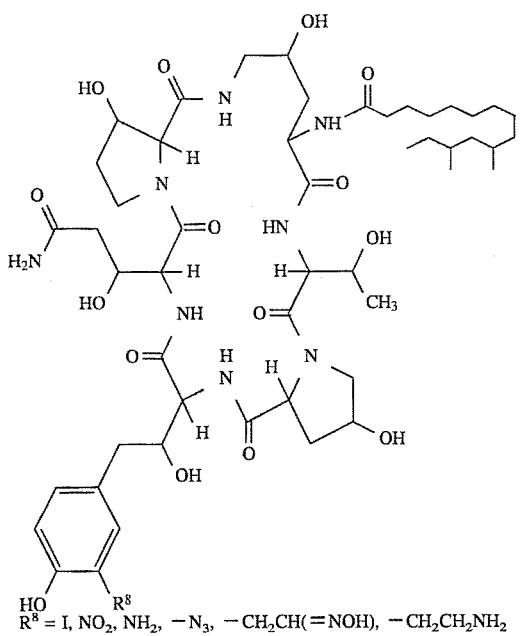

$R^8$ = I, $NO_2$, $NH_2$, $-N_3$, $-CH_2CH(=NOH)$, $-CH_2CH_2NH_2$

Another subset of compounds of the present invention is represented by formula 1-d set forth below.

(SEQ ID NO. 6)                                                          I-d

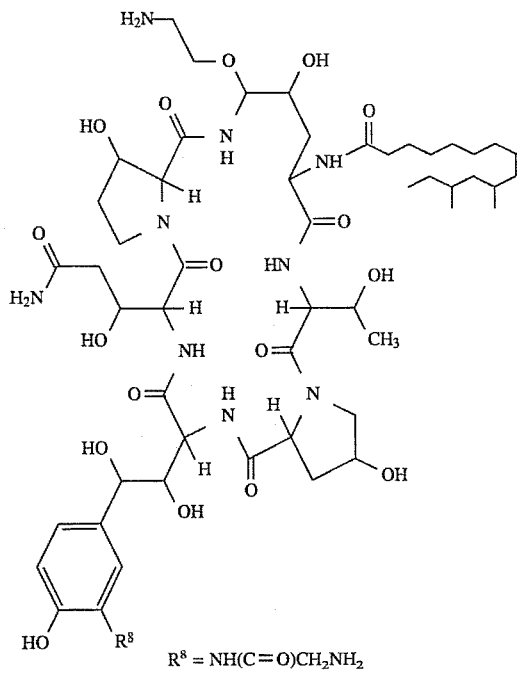

$R^8$ = $NH(C=O)CH_2NH_2$

Another subset of compounds of the present invention is represented by formula 1-e set forth below.

(SEQ ID NO. 7)                                                          I-e

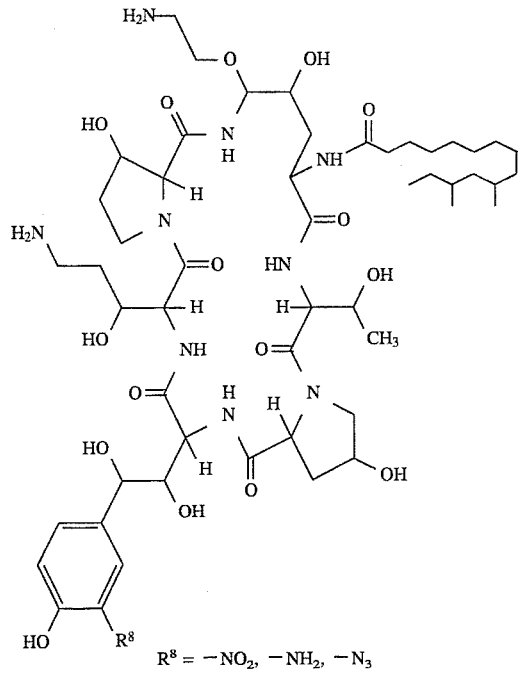

$R^8$ = $-NO_2$, $-NH_2$, $-N_3$

The compounds of formula I and of all subsets thereof are substituted ortho to the homotyrosine phenol group, with the variable $R^8$. $R^8$ is a member selected from the group consisting of: —Cl, —Br, —I, —$NO_2$, —$(CH_2)_{0-4}NR^VR^{VI}$ with $R^V$ and $R^{VI}$ as previously defined, —$N_3$, —$(CH_2)_{0-3}CH(=NOH)$, —$NHC(=O)(CH_2)_{1-6}NH_2$ or —$NHC(=O)(CH_2)_{1-6}NHC(=NH)(CH_2)_{0-3}H$.

In the case where a substituent group pertains to a basic moiety such as amino, alkylamino or imino, where an acid addition salt is possible (e.g. —$NH_3^+Y^-$), Y represents a counterion. Thus, $Y^-$ can represent any of the negatively charged species set forth below.

$Y^-$ may be a negatively charged counterion selected from the group: acetate, adipate, alginate, aspartate, benzoate, benzenesulfonate, bisulfate, bromide, butyrate, citrate, camphorate, camphorsulfonate, chloride, cyclopentanepropionate, digluconate, dodecylsulfate, ethanesulfonate, fumarate, gluconheptanoate, glycerophosphate, hemisulfate, heptanoate, hexanoate, hydrochloride, hydrobromide, hydroiodide, 2-hydroxyethanesulfonate, iodide, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, trifluoroacetate (TFA), tosylate and undecanoate.

The compounds of the present invention are useful per se and in their pharmaceutically acceptable salt and hydrate forms in the treatment of fungal and Pneumocystis infections in animal and human subjects. The term "pharmaceutically acceptable salt and hydrate," refers to those salts and hydrated forms of the compounds of the present invention which would be apparent to the pharmaceutical chemist. i.e., those which are substantially non-toxic and which may favorably effect palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carders. Thus, the present invention is concerned with pharmaceutical compositions and methods of treating infections utilizing as an active ingredient the novel cyclic peptide compounds.

The pharmaceutically acceptable salts referred to above also includes substantially non-toxic acid addition salts. The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

The compounds of the present invention are valuable antifungal agents, which are active against various fungal organisms, and accordingly will likely find utility in human and veterinary medicine. The compounds of the invention are not limited to utility as medicaments; they may be used in all manner of industry, for example: additives to animal feed, preservation of food, disinfectants, and in other industrial systems where control of fungal growth is desired. For example, they may be employed in compositions in concentrations ranging from about 0.01 to about 100 parts of antifungal agent per million parts of solution in order to destroy or inhibit the growth of harmful fungi on medical and dental equipment and as fungicides in industrial applications, for example in water based paints and in the white water of paper mills to inhibit the growth of harmful fungi.

In vitro antifungal activity which is determined in accordance with the protocol set forth below is predictive of in vivo activity, when the compounds are administered to a mammal infected with a susceptible fungal organism.

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carded out in a Yeast Nitrogen Base (Difco) medium with 1 percent dextrose (YNBD).

In a representative assay, a compound of the invention is solubilized in 100 percent dimethyl sulfoxide (DMSO) at an initial concentration of 5 mg/ml. Once dissolved, the drug stock is brought to a concentration of 512 mcg/ml by dilution in water such that the final DMSO concentration is about 10 percent. The solution is dispensed via a multichannel pipette into the first column of a 96-well plate (each well containing 0.075 ml of YNBD), resulting in a drug concentration of 256 mcg/ml. Compounds in the first column are diluted 2-fold across the rows yielding final drug concentrations ranging from 256 mcg/ml to 0.12 mcg/ml.

Four hour broth cultures of organisms to be tested are adjusted using a spectrophotometer at 600 nm to equal a 0.5 McFarland Standard. This suspension is diluted 1:100 in YNBD to yield a cell concentration of $1-5\times10^4$ colony forming units (CFU) per mi.

Aliquots of the suspension (0.075 ml) are inoculated into each well of the microtiter plate resulting in a final cell inoculum of $5-25\times10^3$ CFU/ml and final drug concentrations ranging from 128 mcg/ml to 0.06 mcg/ml. Each assay includes one row for drug-free control wells and one row for cell-free control wells.

After 24 hours of incubation, the microtiter plates are gently shaken on a shaker to resuspend the cells. The MIC-2000 inoculator is used to transfer a 1.5 microliter sample from each well of the 96-well microtiter plate to a single reservoir inoculum plate containing Sabouraud dextrose agar (SDA). The inoculated SDA plates are incubated for 24 hours at 35° C.

The following data pertains to compounds of formula I-a with $R^8$ defined below:

| $R^8$ | MFC (mcg/mL) (C. albicans MY1055) |
|---|---|
| Cl | 1 |
| $NO_2$ | 8 |
| $NH_2$ | 2 |
| $N_3$ | 0.50 |
| $NHC(=O)CH_2NH_2$ | 0.25 |
| $NHC(=O)CH_2CH_2NH_2$ | 0.25 |
| $NHC(=O)CH_2CH_2NHC(=NH)CH_3$ | 0.25 |

The following data pertains to compounds of formula I-b with $R^8$ defined below:

| $R^8$ | MFC (mcg/mL) (C. albicans MY1055) |
|---|---|
| $NH_2$ | 1 |
| $NO_2$ | 8 |

The following data pertains to compounds of formula I-c with $R^8$ defined below:

| $R^8$ | MFC (mcg/mL) (C. albicans MY1055) |
|---|---|
| I | 0.5 |
| $NO_2$ | 2 |
| $NH_2$ | 2 |
| $N_3$ | 4 |
| $CH_2CH(=NOH)$ | 0.5 |

The following data pertains to compounds of formula I-d with $R^8$ defined below:

| $R^8$ | MFC (mcg/mL) (C. albicans MY 1055) |
|---|---|
| $-NHC(=O)CH_2NH_2$ | 0.5 |

The following data pertains to compounds of formula I-e with $R^8$ defined below:

| $R^8$ | MFC (mcg/mL) (C. albicans MY1055) |
|---|---|
| $NH_2$ | 0.25 |
| $N_3$ | 0.25 |

The activity of the compounds of the invention can also be demonstrated through an in vivo assay, as follows:

Growth from an overnight SDA culture of *Candida albicans* MY 1055 is suspended in sterile saline and the cell concentration determined by hemocytometer count and the cell suspension adjusted to $3.75\times10^5$ cells/mi. 0.2 ml of this suspension is administered I.V. in the tail vein of mice so that the final inoculum is $7.5\times10^4$ cells/mouse. The assay is then carried out by administering aqueous solutions of the compounds at various concentrations intraperitoneally (I.P.) twice daily (b.i.d.) for four consecutive days to 18–20 gram female DBA/2 mice, which previously had been infected with *Candida albicans* in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 mls of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units per gram of kidney tissue.

Representative activities are listed below. The following data pertains to compounds of formula I-a with $R^8$ defined below:

| $R^8$ | $ED_{99}$ (mg/kg) |
|---|---|
| —$NH_2$ | 3.0 |
| —$NHC(=O)CH_2CH_2NH_2$ | <0.78 |

The compounds of the present invention may also be used to inhibit or alleviate *Pneumocystis carinii* infections in immunocompromised patients. *Pneumocystis carinii* may become opportunistic in mammals which are immunocompromised, such as in AIDS patients. The efficacy of the compounds for therapeutic or anti-infective purposes may be demonstrated in studies on immunosuppressed rats.

In a representative study, Sprague-Dawley rats (weighing approximately 250 grams) are immunosuppressed with dexamethasone in the drinking water (2.0 mg/L) and maintained on a low protein diet for seven weeks to induce the development of Pneumocystis pneumonia from a latent infection. Before drug treatment, two rats can be sacrificed to confirm the presence of *Pneumocystis carinii* pneumonia (PCP).

Five rats (weighing approximately 150 grams) are injected twice daily for four days subcutaneously (sc) with a compound of the invention in 0.25 ml of vehicle (water). A vehicle control is also carried out. All animals are continued on dexamethasone in the drinking water and a low protein diet during the treatment period. At the completion of the treatment, all animals are sacrificed, the lungs are removed and processed, and the extent of disease determined by microscopic analysis of stained slides. An $ED_{90}$ is thus obtained where at least 90% of the cysts present in the control animals are inhibited in the treated animals.

Representative activities are listed below. The following data pertains to compounds of formula I-a with $R^8$ defined below:

| $R^8$ | $ED_{90}$ (mg/kg) |
|---|---|
| —$NH_2$ | 0.075 |
| —$NHC(=O)CH_2CH_2NH_2$ | 0.075 |

The following data pertains to compound of formula I-d with $R^8$ defined below:

| $R^8$ | $ED_{90}$ (mg/kg) |
|---|---|
| —$NHC(=O)CH_2NH_2$ | 0.019 |

With respect to Pneumocystis, the compounds of the invention can thus be used to treat an infection which has been diagnosed or the compound can be used in those mammalian patients who are immunocompromised and predisposed to developing a Pneumocystis infection, to prevent the organism from becoming pathogenic and causing an infection. As used herein, both treatment modalities are included in the invention.

The compounds of this invention may be used in a variety of pharmaceutical preparations. The pharmaceutical composition is comprised of a compound of formula I in combination with a pharmaceutically acceptable carrier.

The compound may be employed in solid, powder or crystalline form, in liquid solution, or in suspension. They may be administered by a variety of means; those of principal interest include: topically, orally, parenterally by injection (intravenously or intramuscularly) and for purposes of treating Pneumocystis pneumonia, via inhalation as a powder or liquid.

Compositions for injection, one preferred route of delivery, may be prepared in unit dosage form in ampoules, or in multidose containers. The injectable compositions may take such forms as suspensions, solutions or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water.

Topical applications are also preferred for the treatment of candidiasis, and may be formulated in hydrophobic or hydrophilic bases as ointments, creams, lotions, paints, or powders.

Compositions administered orally may take such forms as tablets, capsules, oral suspensions and oral solutions. The oral compositions may utilize conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the medical arts. Another factor influencing the precise dosage regimen, apart from the nature of the infection and peculiar identity of the individual being treated, is the molecular weight of the compound.

The compositions for human use per unit dosage, whether liquid or solid, may contain from about 0.01% to as high as about 99% of active material, the preferred range being from about 10–60%. The composition will generally contain from about 0.1 mg to about 2.0 g of the active ingredient; however, in general, it is preferable to employ a dosage amount in the range of from about 1 mg to 500 mg.

In parenteral administration, the unit dosage will typically include the pure compound in sterile water solution or in the form of a soluble powder intended for solution, which can be adjusted to neutral pH and isotonic.

The preferred methods of administration of the Formula I compounds include oral and parenteral, e.g., i.v. infusion, i.v. bolus and i.m. injection.

For adults, about 0.5–50 mg of the compound per kg of body weight given one to four times daily is preferred. The preferred dosage is 2.5 mg to 1000 mg of the compound given one to four times per day. More specifically, for mild infections a dose of about 2.5 to 100 mg administered two or three times daily is recommended. For moderate infections against highly susceptible organisms a dose of about 500 mg three or four times daily is recommended. For severe, life-threatening infections against organisms at the upper limits of sensitivity to the compound, a dose of about 1000–2000 mg three to four times daily may be recommended.

For the treatment of vaginal candidiasis, the compound may be administered in a predetermined amount which is not necessarily adjusted for body weight, e.g., 50 mg given once daily for seven to ten days. Typically compounds used for the treatment of vaginal candidiasis will be formulated in a cream or suppository form which is administered intravaginally.

For the treatment of *Pneumocystis carinii* pneumonia, the compound may preferably be administered via the pulmonary route, such as through the use of an intermittent positive pressure breathing (IPPB) apparatus, or in the form of an aerosol or unit dose spray powder. Typically the compound is administered three or four times daily, in an amount sufficient to treat the infection which has developed, or to prevent the development of infection.

As used herein, prevention of a Pneumocystis infection in an immunocompromised mammalian patient involves administering a compound in accordance with formula I to the patient prior to the development of symptoms, based upon an expectation that the immunocompromised patient is more likely to develop a Pneumocystis infection than an immune competent patient. Immunocompromised patients are readily recognized by the skilled artisan by reviewing the overall condition of the patient, taking into account blood chemistry and cellular component values, e.g., the CD4 lymphocyte count.

The invention is further illustrated in connection with the following non-limiting examples.

PREPARATIVE EXAMPLE I (SEQ ID NO. 8)

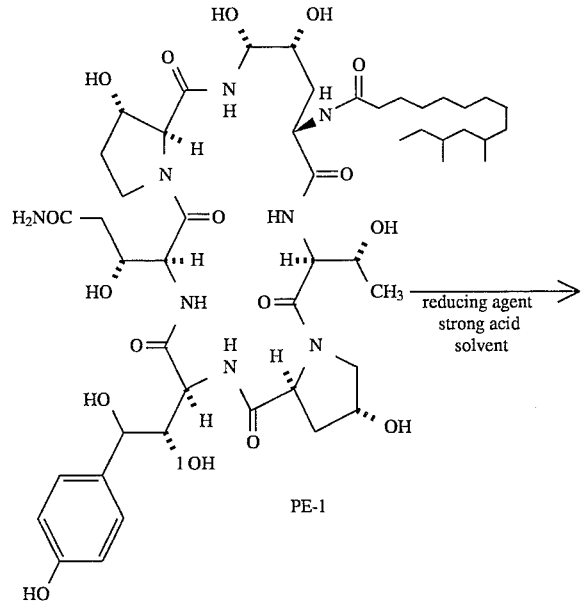

PE-1

-continued
PREPARATIVE EXAMPLE I (SEQ ID NO. 9)

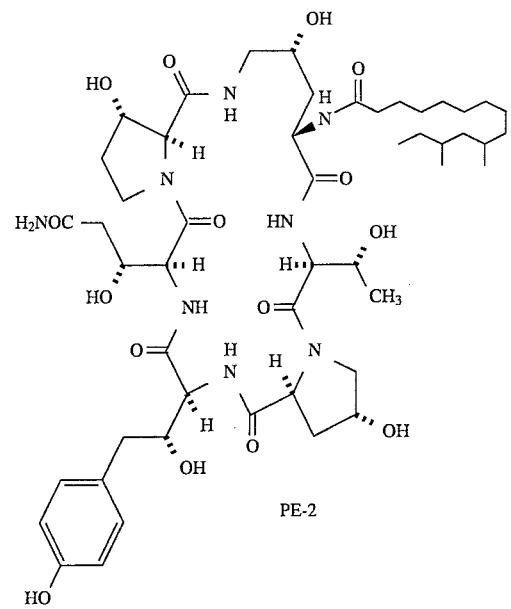

PE-2

The starting material for Example 1 below is obtained in accordance with the procedures set forth in U.S. Ser. No. 901,720 filed on Jun. 15, 1992, and in Balkovec, et al. Tetrahedron Letters, Vol. 33 pages 4529–4532 (1992) (identified as Compound 6d). Briefly, compound PE-1 is combined with trifluoroacetic acid. Sodium cyanoborohydride is added and the solution is stirred at room temperature. The volatiles are removed in vacuo to produce a solid, which is purified by reverse phase HPLC, eluting with water:acetonitrile (45/55) to obtain compound PE-2 as a white solid after lyophilization.

PREPARATIVE EXAMPLE II (SEQ ID NO. 10)

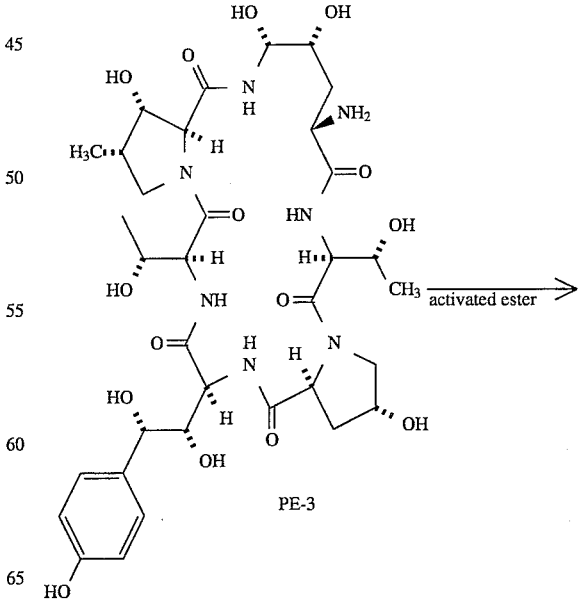

PE-3

PREPARATIVE EXAMPLE II -continued (SEQ ID NO. 11)

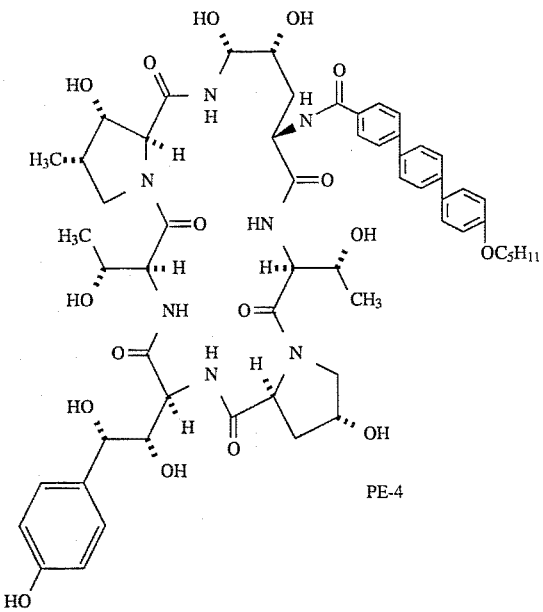

PE-4

4-(4-n-Pentoxyphenyl)bromobenzene

To a stirred solution of 4-(4-bromophenyl)phenol (25.5 g, 0.102 mol) in 400 mL of dimethylsulfoxide was added 2.5N NaOH (40.9 mL, 0.102 mol) followed by n-pentyl bromide (12.7 mL, 0.102 mol). The resulting mixture was heated at 70° C. for a period of 18 h. After cooling, the yellow solution was partitioned between ethyl acetate (1000 mL) and water (500 mL). The organic phase was washed with water (3×) and brine and dried with magnesium sulfate. The solvent was removed in vacuo to give 4-(4-n-pentoxyphenyl)bromobenzene (30.9 g).

$^1$H NMR (400 MHz, DMSO-$d_6$) d0.93 (t, J=7.2 Hz, 3H), 1.41 (m, 4H), 1.79 (m, 2H), 3.97 (t, J=6.6 Hz, 2H), 6.94 (d, J=8.8 Hz, 2H), 7.39 (d, J=8.6 Hz, 2H), 7.45 (d, J=8.8 Hz, 2H), 7.51 (d, J=8.6 Hz, 2H).

4-(4-n-Pentoxyphenyl)phenylboronic acid

To a stirred suspension of 4-(4-n-pentoxyphenyl)bromobenzene (1.0 g, 3.13 mmol) in anhydrous tetrahydrofuran (20 mL) at −78° C. under a nitrogen atmosphere was added n-butyllithium in hexanes (2.5M, 1.32 mL, 3.30 mmol). After a period of 15 min, triisopropylborate (760 mL, 3.30 mmol) was added. Stirring at −78° C. was continued for 15 min and then at 25° C. for 40 min. The mixture was acidified with 0.5N HCl (20 mL) and then partitioned between ether (50 mL) and water (40 mL). The organic phase was washed with water (3×) and brine and dried with magnesium sulfate. The solvent was removed in vacuo to give 4-(4-n-pentoxyphenyl)phenylboronic acid (750 mg) as a white solid.

$^1$H NMR (400 MHz, DMSO-$d_6$) d0.89 (t, J=7.2 Hz, 3H), 1.38 (m, 4H), 1.72 (m, 2H), 3.99 (t, J=6.5 Hz, 2H), 6.99 (d, J=8.8 Hz, 2H), 7.57 (d, J=8.2 Hz, 2H), 7.60 (d, J=8.8 Hz, 2H), 7.83 (d, J=8.2 Hz, 2H).

4-(n-pentyloxyphenyl)-4'-methoxycarbonylbiphenyl

To a stirred solution of 4-(4-n-pentyloxyphenyl)phenylboronic acid (1.45 g, 5.11 mmol) and methyl 4-bromobenzoate (1.21 g, 5.62 mmol) in dimethylformamide (12 mL) was added triethylamine (1.43 mL, 10.21 mmol) followed by triphenylphosphine (536 mg, 2.04 mmol) and palladium(II) acetate (230 mg, 1.02 mmol). The reaction was heated at 80° C. for a period of 18 h. The cooled mixture was partitioned between methylene chloride and water. The organic phase was washed with 1M sodium bicarbonate, water (2×) and brine, dried over magnesium sulfate and filtered through a bed of celite. The solvent was removed in vacuo to give crude product which was purified by pre-adsorption flash silica gel chromatography to provide 4-(n-pentyloxyphenyl)-4'-methoxycarbonylbiphenyl (220 mg).

$^1$H NMR (400 MHz; CDCl$_3$) d0.93 (t, J=7.1 Hz, 3H), 1.41 (m, 4H), 1.83 (m, 2H), 3.93 (s, 3H), 3.99 (t, J=6.6 Hz, 2H), 6.97 (d, J=8.8 Hz, 2H), 8.10 (d, J=8.5 Hz, 2H).

MS (EI)=374

4-(n-pentyloxyphenyl)-4'-carboxybiphenyl

A mixture of 4-(n-pentyloxyphenyl)-4'-methoxycarbonylbiphenyl (220 mg, 0.58 mmol) and 5N sodium hydroxide (1.17 mL, 5.88 mmol) in tetrahydrofuran (20 mL) was heated at 80° C. under reflux for a period of 18 h. The cooled mixture was acidified with 1N hydrochloric acid (35 mL) and partitioned between ethyl acetate and water. The organic suspension was washed with water (3×) and brine. The organic layer was then filtered to give the carboxylic acid, 4-(n-pentyloxyphenyl)- 4'-carboxybiphenyl (210 mg).

$^1$H NMR (400 MHz; DMSO-$d_6$) d0.90 (t, J=7.1 Hz, 3H), 1.37 (m, 4H), 1.73 (m, 2H), 4.0 (t, J=6.6 Hz, 2H), 7.02 (d, J=8.9 Hz, 2H), 8.02 (d, J=8.5 Hz, 2H).

MS (EI)=360.2

Acylation of the Echinocandin B Nucleus

The carboxylic acid as prepared above (572 mg) was dissolved in 15 mL of dry N,N-dimethylformamide. Pentafluorophenol (586 mg) and dicyclohexylcarbodiimide (492 mg) were added and the mixture was stirred overnight. Echinocandin B nucleus (846 mg), 5 mL of N,N-dimethylformamide used as a rinse and diisopropylethylamine (0.41 mL) were added. The mixture was stirred for 18 hours at which time it was diluted with water and acetonitrile. Purification by preparative HPLC (DELTA PAK C18, gradient: 40% CH$_3$CN/60% H$_2$O to 55% CH$_3$CN/45% H$_2$O, λ=210, 277 nm) gave PE-4 (610 mg) as a solid.

FAB MS (M+Na$^+$) 1162.

EXAMPLE I (SEQ ID NO. 12)                                               Ex-1

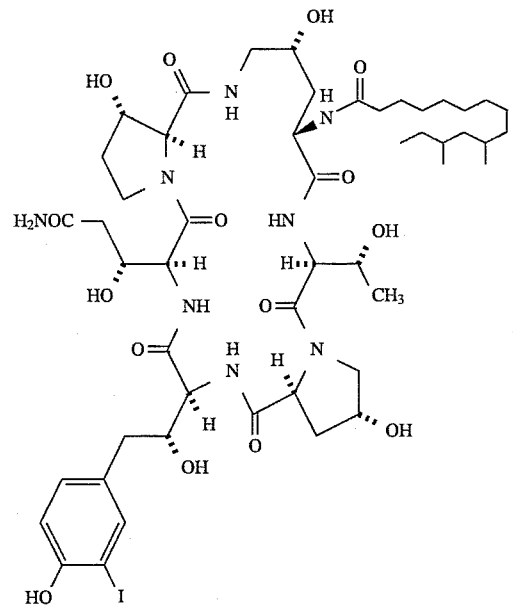

A solution of compound PE-2 (50mg, 0.05mmol) from Preparative Example 1 and sodium iodide (7.5 mg, 0.05 mmol) in methanol was cooled to 0° C. Aqueous sodium hypochlorite (5.25% w/v, 0.0709 mL, 0.05 mmol) was then added dropwise. The resulting yellow solution was allowed to stir at 0° C. for 20 minutes. Analytical HPLC (50% CH$_3$CN/50% H$_2$O, 2 mL/min, C8 ZORBAX, 4.6×250 mm, λ=210, 277 nm) indicated complete consumption of starting material. The reaction mixture was treated with 1 mL of 10% aqueous sodium thiosulfate and the pH was adjusted to 7 with 2N HCl. The resulting solution was diluted to about 5 mL with water, filtered, and injected onto a preparative HPLC column (C8 ZORBAX, 50% CH$_3$CN/ H$_2$O, λ=210, 277 nm). Lyophilization of the appropriate fractions as determined by analytical HPLC gave 23 mg of of Compound Ex-1 as a white solid.

Partial $^1$H NMR (400 MHz, CD$_3$OD): δ7.57 (s, 1H), 7.04 (dd, 1H), 6.75 (dd, 1H), 5.09 (d, 1H), 2.99 (dd, 1H).

FAB MS (M+1): 1158.

EXAMPLE II (SEQ ID NO. 13)                                            Ex-2

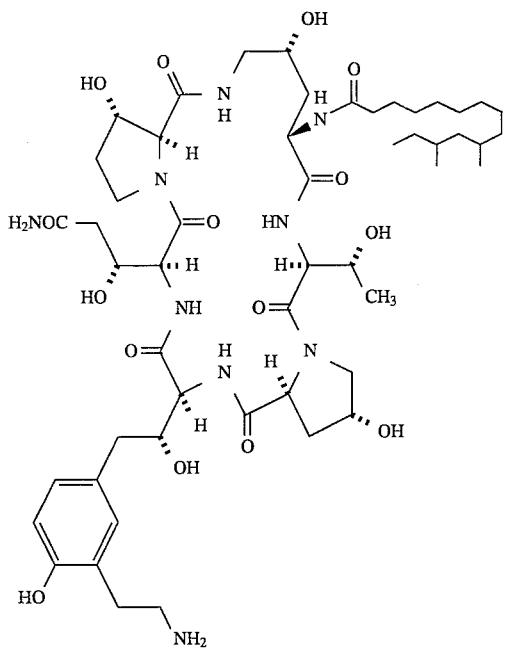

Part A. Allylation

To a solution of Compound Ex-1 (100 mg, 0.086 mmol) in 1-methyl-2-pyrrolidinone (1 mL) was added tetrakis(triphenylphosphine) palladium(0) (10 mg, 0.009 mmol) followed by allyltributyltin (0.040 mL, 0.13 mmol). Lithium chloride (7 mg, 0.17 mmol) was then added and the resulting pale yellow solution was stirred at 60° C. for 2 hours. Analytical HPLC (C8 ZORBAX, 45% H$_2$O/55% CH$_3$CN, λ=210, 277 nm) showed conversion of starting material to product. The reaction mixture was diluted with water to about 5 mL, filtered and injected onto a preparative HPLC column (C8 ZORBAX, 50% CH$_3$CN/50% H$_2$O, λ=210, 277 nm). The appropriate fractions as determined by analytical HPLC were combined and lyophilized to give 54 mg of the ortho-allylated phenol (Compound I-c, R$^8$=—CH$_2$CH=CH$_2$) as a white solid.

Partial $^1$H NMR (400 MHz, CD$_3$OD): δ6.91(s, 1H), 6.87(dd, 1H), 6.69(dd, 1H), 5.09(d, 1H), 2.99(dd, 1H).

FAB MS (M+Li): 1080.0.

Part B. Ozonolysis

A solution of the product from part A above, (70 mg, 0.065 mmol) in 3 mL of methanol was added to a saturated solution of ozone in dichloromethane at −78° C. (2.5 mL, ~0.04M, 0.098 mmol). The resulting solution was stirred at −78° C. for 15 minutes and was then allowed to warm to room temperature. Methyl sulfide (1 mL, 13 mmol) was added and the reaction mixture was stirred overnight. Analytical HPLC (45% H$_2$O/55% CH$_3$CN, C8 ZORBAX, λ=210, 277 nm) showed complete reaction. The solution was diluted to about 5 mL with water and injected onto a preparative HPLC column (C8 ZORBAX, 50% CH$_3$CN/ 50% H$_2$O, λ=210, 277 nm). Lyophilization of the appropriate fractions as determined by analytical HPLC gave 47 mg of the aldehyde (Compound I-c, R$^8$=—CH$_2$CH=O) as a white solid.

Partial $^1$H NMR (400 MHz, CD$_3$OD): δ6.95 (d), 6.90 (dd), 6.69 (dd), 5.09 (d), 4.79 (m), 2.99 (dd, 1H), 2.89 (dd, 1H), 2.79 (dd, 1H).

FAB MS (M+Li): 1082.0.

Part C. Reductive Amination

To a solution of the product from part B above (11.4 mg, 0.01 mmol) in 0.5 mL of methanol was added ammonium acetate (7.7 mg, 0.1 mmol) and sodium cyanoborohydride (1 mg, 0.016 mmol). The resulting mixture was stirred at room temperature overnight. The reaction, mixture was then diluted to about 5 mL with water, filtered and injected onto a preparative HPLC column (C8 ZORBAX, 50% CH$_3$CN/ 50% H$_2$O/0.1% TFA, λ=210, 277 nm). Lyophilization of the appropriate fractions gave 1.2 mg of Compound Ex-2 as a white solid.

Partial $^1$H NMR (400 MHz, CD$_3$OD): δ6.95 (dd, 1H), 6.89 (s, 1H), 6.75 (dd, 1H), 5.09 (m, 1H), 3.19(t, 2H), 2.99 (dd, 1H), 2.95 (t, 2H).

FAB MS (M+Li): 1083.2.

EXAMPLE III (SEQ ID NO. 14)                                            Ex-3

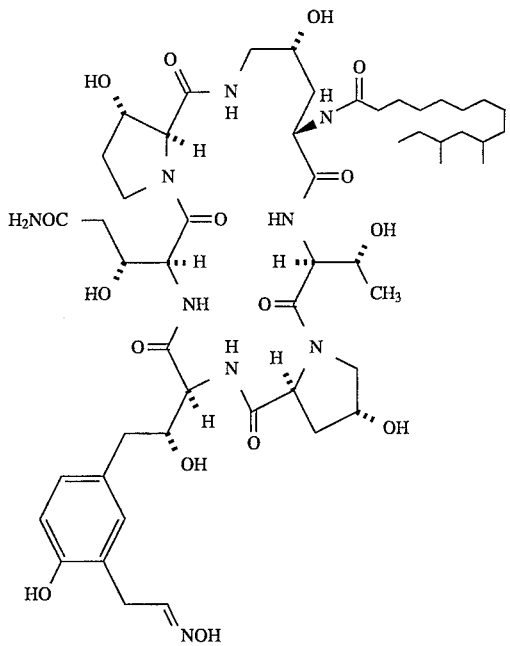

To a solution of the product from part B, example II, above (25 mg, 0.023 mmol) in 0.5 mL of pyridine was added hydroxylamine hydrochloride (5 mg, 0.072 mmol). The resulting solution was stirred at room temperature for 2 hours. Analytical HPLC (45% H₂O/55% CH₃CN, C8 ZORBAX, λ=210, 277 nm) showed complete conversion of starting material to one product. The reaction mixture was concentrated by rotary evaporation, diluted with 5 mL of 1:1 CH₃CN/H₂O, filtered, and injected onto a preparative HPLC column (50% H₂O/ 50% CH₃CN, C8 ZORBAX, λ=210, 277 nm). Lyophilization of the appropriate fractions as determined by analytical HPLC gave 15.8 mg of Compound Ex-3 as a mixture of geometric isomers.

Partial $^1$H NMR of mixture (400 MHz, CD₃OD): δ6.92, 6.91 (dd), 6.90 (s, 1H), 6.74, 6.71 (dd, 1H), 5.09 (d, 1H), 3.61(d, 2H), 3.41 (d, 2H), 2.99 (dd, 1H).

FAB MS (M+Li): 1097.0.

EXAMPLE IV (SEQ ID NO. 15)    Ex-4

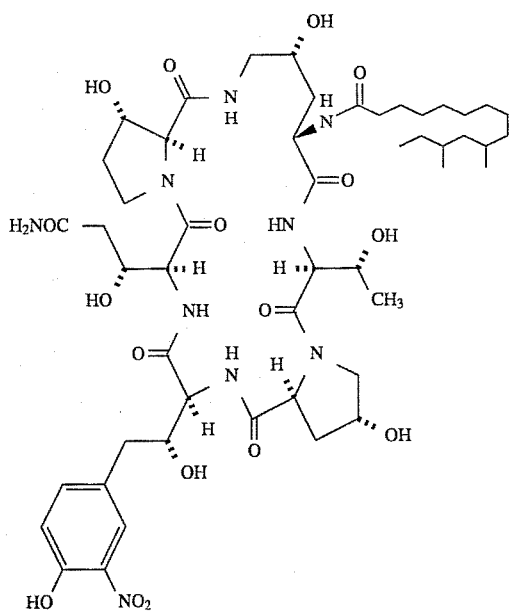

Compound PE-2 from Preparative Example 1 (309 mg, 0.299 mmol) was dissolved in 4 mL of absolute ethanol. Iron (III) nitrate nonahydrate (97 mg, 0.240 mmol) was added and the resultant solution was heated to 60° C. After 12 h of stirring, the mixture was cooled and the volatiles were removed by rotary evaporation at reduced pressure. The residue was dissolved in 55% aqueous acetonitrile and filtered. Purification by preparative reverse phase HPLC (C8 ZORBAX, 45% H₂O/ 55% CH₃CN, λ=210, 277 nm) gave 148 mg of Compound Ex-4 after lyophilization of the appropriate fractions.

Partial $^1$H NMR (400 MHz, CD₃OD): δ7.94 (d, 1H), 7.49 (dd, 1H), 7.08 (d, 1H), 5.11 (d, 1H), 4.98 (d, 1H), 2.99 (dd, 1H), 1.17 (d, 3H).

FAB MS (M+Li): 1083.

EXAMPLE V (SEQ ID NO. 16)    Ex-5

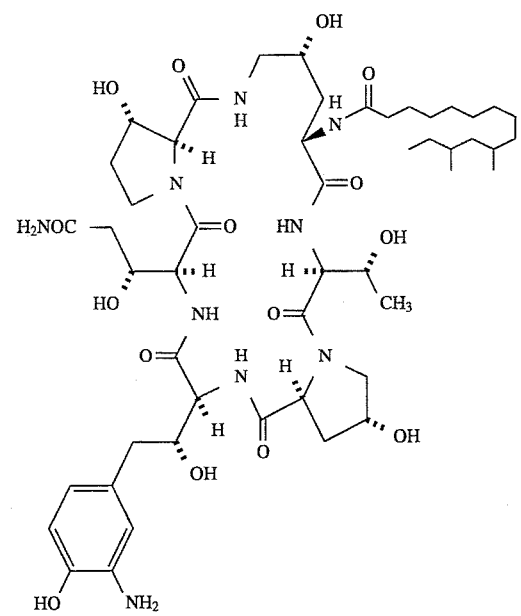

10% Palladium on charcoal was suspended in 1 mL of deionized water and sodium borohydride (10.5 mg, 0.279 mmol) was added. After stirring for 1 min, a solution of Compound Ex-4 (150 mg, 0.139 mmol) in 4 mL of methanol was added dropwise. The yellow color of the solution persisted after several minutes therefore approximately 5 mg of sodium borohydride was added. Stirring was continued for 15 min. The reaction was centrifuged to remove the catalyst and the clear solution was filtered through a 0.2 micron filter frit. The solution was kept under nitrogen. The volume was reduced by passing a stream of dry nitrogen over the solution. The mixture was purified by preparative HPLC (C8 ZORBAX, 50% H₂O/ 50% CH₃CN, λ=210, 277 nm). Lyophilization of the appropriate fractions gave 105 mg of compound Ex-5 as a slightly dark solid.

Partial $^1$H NMR (400 MHz, CD₃OD): δ6.59 (m, 2H), 6.41 (dd, 1H), 5.09 (d, 1H), 4.97 (d, 1H), 2.99 (dd, 1H), 1.18 (d, 3H).

FAB MS (M+Li): 1053.

EXAMPLE VI (SEQ ID NO. 17)    Ex-6

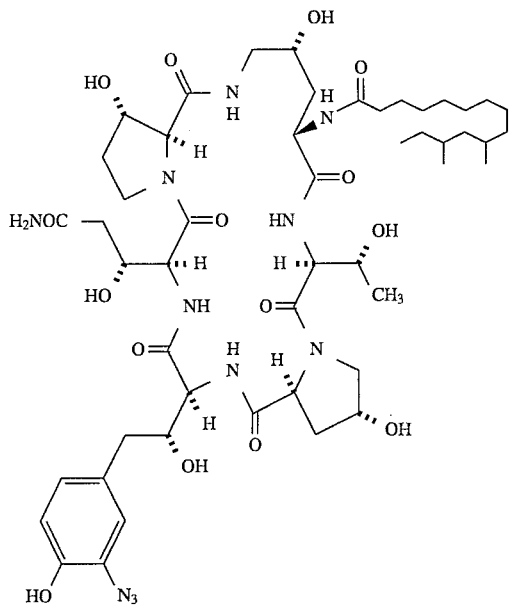

Compound Ex-5 (20 mg, 0.019 mmol) was dissolved in 0.1N hydrochloric under an atmosphere of nitrogen. The solution was cooled to 0° C. and a solution of 1N sodium nitrite (0.0209 mL, 0.0209 mmol) was added. After stirring for 15 minutes, a solution of 1N potassium azide (0.038 mL, 0.038 mmol) was added and the reaction was stirred an additional 15 minutes. The acidity of the solution was adjusted to approximately pH 5 by the addition of 0.2 mL of 1N sodium acetate amd the vessel was removed from the ice bath and stirred for 1 h to give an orange heterogeneous mixture. The solid was removed by filtration and after washing with water was dissolved in methanol. The methanol was removed by rotary evaporation at reduced pressure to give a dark semi-solid. Purification by preparative HPLC (50% $H_2O$/ 50% $CH_3CN$, C8 ZORBAX, $\lambda$=210, 277 nm) and lyophilization of the appropriate fractions gave 12 mg of Compound Ex-6 as a white solid.

Partial $^1H$ NMR (300 MHz, $CD_3OD$): $\delta$6.89 (d, 1H), 6.86 (s, 1H), 6.77 (d, 2H), 5.14 (d, 1H), 5.02 (m, 1H), 3.02 (dd, 1H), 1.21 (d, 3H).

FAB MS (M+Li-$N_2$): 1051.

IR (KBr): 2115 $cm^{-1}$

UV (aqueous $CH_3CN$): $\lambda_{max}$ (nm)=200, 250, 296.

EXAMPLE VII (SEQ ID NO. 18)    Ex-7

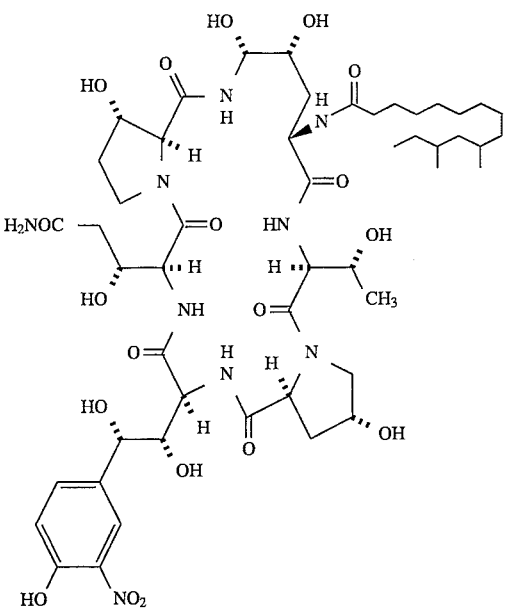

To a stirred solution of pneumocandin $B_0$ (0.496 g, 0.466 mmol) in 15 mL of glacial acetic acid was added 1N $NaNO_2$ (1.0 mL, 0.001 mol). After stirring at room temperature for 18 h the solvent was removed by rotary evaporation to yield an orange semi-solid. The crude product was dissolved in a minimal amount of aqueous methanol, filtered and purified by preparative reverse phase HPLC (C8 ZORBAX, 55% water/45% acetonitrile, $\lambda$=210, 277 nm). The appropriate fractions were combined, frozen and lyophilized to give 0.235 g of Compound Ex-7 as a yellow amorphous solid.

Partial $^1H$ NMR (400 MHz, $CD_3OD$): $\delta$8.01 (d, I H), 7.69 (dd, 1H), 7.14 (d, 1H), 5.28 (d, 1H), 5.09 (d, 1H), 4.98 (d, 1H), 1.15 (d, 3H).

FAB MS (M+Li): 1116.

EXAMPLE VIII (SEQ ID NO. 19)  Ex-8

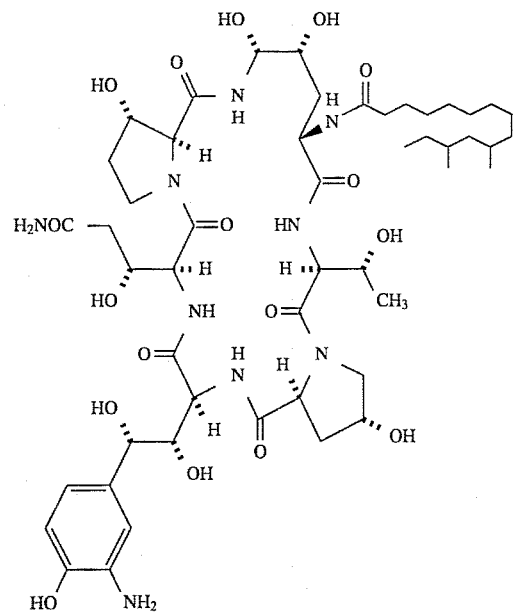

Compound Ex-7 (0.126 g, 0.114 mmol) was dissolved in 4 mL of methanol. After flushing the reaction vessel with $N_2$, 35 mg of 10% Pd on charcoal was added followed by 1 mL of distilled water. Sodium borohydride (8.6 mg, 0.227 mmol) was added to the reaction mixture in 2 portions over 5 min. Approximately 0.3 mL acetic acid was cautiously added to the heterogeneous mixture. After stirring for 1 h, the reaction was filtered through a 0.2 micron filter. The crude product was purified by preparative reverse phase HPLC (C8 ZORBAX, 50% water/50% acetonitrile, λ=210, 277 nm). The appropriate fractions were combined, frozen and lyophilized to give 0.081 g of Compound Ex-8 as an off-whim amorphous solid.

Partial $^1$H NMR (400 MHz, $CD_3OD$): δ6.73 (d, 1H), 6.64 (d, 1H), 6.51 (dd, 1H), 5.28 (d, 1H), 5.09 (m, 1H), 4.98 (d, 1H), 1.18 (d, 3H).

FAB MS (M+Li): 1086.

EXAMPLE IX (SEQ ID NO. 20)  Ex-9

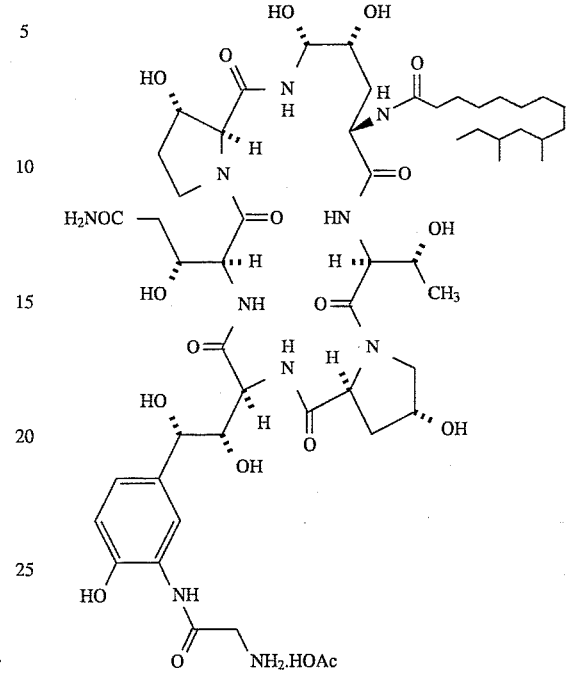

Part A. Conjugation

Compound Ex-8 (68 mg, 0.063 mmol) and pentafluorophenyl N-benzyloxycarbonylglycinate (35 mg, 0.0944 mmol) were dissolved in 0.5 mL of N-methylpyrrolidinone. The mixture was stirred for 24 h at room temperature. Purification was accomplished by preparative HPLC (C8 ZORBAX, 55% water/45% acetonitrile, λ=210, 277 nm). The appropriate fractions were combined, frozen and lyophilized to give 40 mg of the N-protected glycyl conjugate (Compound I-a, $R^8$=—NH(C=O)$CH_2$NH(C=O)O$CH_2C_6H_5$) as an amorphous solid.

FAB MS (M+Li): 1278.

Part B. Hydrogenolysis

The product from Part A above (40 mg, 0.031 mmol) was dissolved in 2 mL of glacial acetic acid. Next, 2 mL of deionized water was added followed by 20 mg of 10% palladium on charcoal. The vessel was flushed with hydrogen gas and stirring under one atmosphere of hydrogen was continued for 2 h. The catalyst was removed by filtration and the volatiles were removed by rotary evaporation under reduced pressure. The residue was dissolved in a small volume of water, frozen and lyophilized to give 35 mg of Compound Ex-9 as an amorphous solid.

Partial $^1$H NMR (400 MHz, CD$_3$OD): δ7.92 (d, 1H), 6.97 (dd, 1H), 6.84 (d, 1H), 5.28 (d, 1H), 5.08 (m, 1H), 4.97 (d, 1H), 1.18 (d, 3H).

FAB MS (M+Li): 1143.8.

EXAMPLE X (SEQ ID NO. 21)　　　　　　　　　　　　　　Ex-10

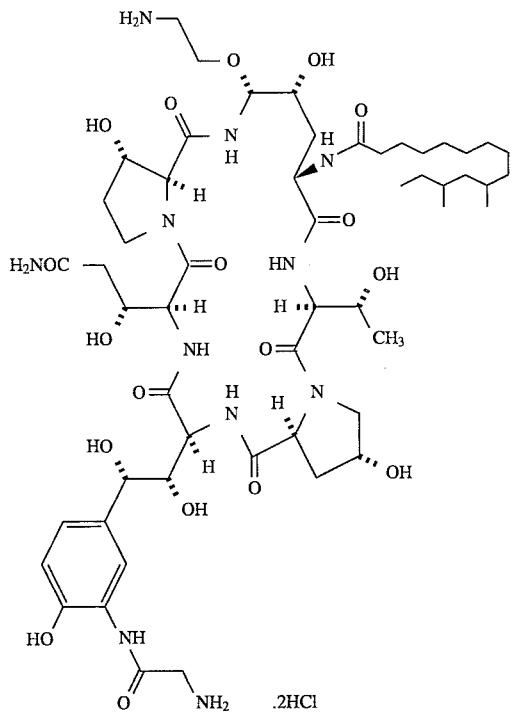

Part A. Etherification

The adduct from Part A Example IX above (400 mg, 0.315 mmol) was dissolved in 40 mL of p-dioxane containing 4 mL of N,N-dimethyl-dimethylformamide. N-Benzyloxycarbonylethanolamine (3.03 g, 15.7 mmol) was added followed by (+)-camphorsulfonic acid (88 mg). Stirring was continued at room temperature for 22 h. The reaction was quenched with approximately 2 mL of saturated sodium hydrogen carbonate solution. The volatiles were removed by concentration at reduced pressure and the mixture purified by preparative HPLC (C18 ZORBAX, 60% water/40% acetonitrile to water/60% acetonitrile, λ=210, 277 nm). The appropriate fractions were combined, frozen and lyophilized to give 0.30 g of the bis-benzyloxycarbonyl-protected product.

Part B. Hydrogenolysis

The adduct from Part A Example X above (0.30 g, 0.21 mmol) was dissolved in 20 mL of glacial acetic acid. To the flask was added 0.11 g of 10% palladium on charcoal. The vessel was flushed with nitrogen followed by hydrogen gas. The reaction was stirred rapidly under one atmosphere of hydrogen gas for 1.5 h. The catalyst was removed by filtration through a 0.45 micron frit. The catalyst was washed with a small amount of 75% aqueous acetic acid. The filtrate was concentrated to about 6 mL under reduced pressure and purified by preparative reverse phase HPLC (C18 ZORBAX, 60% water/40% acetonitrile/0.1% trifluoroacetic acid, λ=220, 286 nm). The appropriate fractions were lyophilized and dissolved in 10 mL of 0.5N hydrochloric acid and lyophilized. The residue was repurified by preparative HPLC (C18 ZORBAX, 60% water/40% acetonitrile, λ=220, 286 nm) and the appropriate fractions lyophilized to yield 95 mg of Compound Ex-10 as a dihydrochloride salt.

Partial $^1$H NMR (400 MHz, CD$_3$OD): δ7.94 (d, 1H), 6.98 (dd, 1H), 6.84 (d, 1H), 5.27 (d, 1H), 5.10 (m, 1H), 5.01 (d, 1H), 3.12 (t, 2H), 1.16 (d, 3 H).

FAB MS (M+Li): 1186.6.

EXAMPLE XI

Ex-11

(SEQ ID NO. 22)

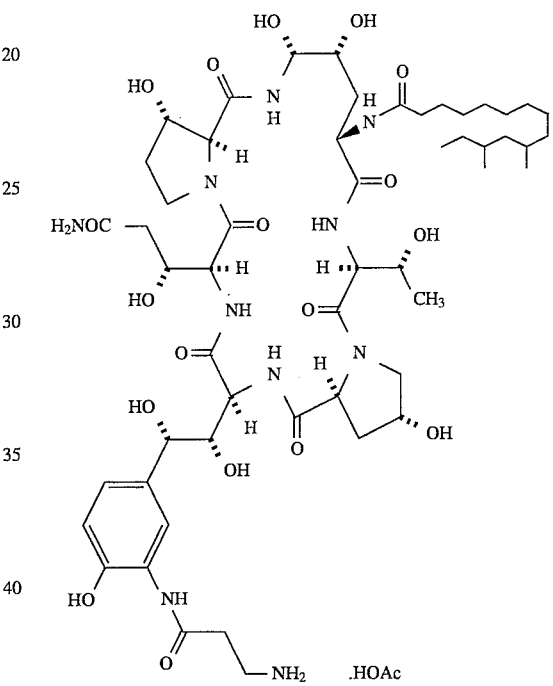

Part A. Conjugation

Compound Ex-8 (40 mg, 0.037 mmol) and pentafluorophenyl N-benzyloxycarbonyl-β-alaninate (15.2 mg, 0.0390 mmol) were dissolved in 1.0 mL of N,N-dimethylformamide (DMF). The mixture was stirred for 60 h at room temperature. The DMF was removed by rotary evaporation at reduced pressure. Purification of the residue was accomplished by preparative HPLC (C8 ZORBAX, 45% water/55% acetonitrile, λ=230, 277 nm). The appropriate fractions were combined, frozen and lyophilized to give 25 mg of the desired conjugate (Compound I-a, R$^8$=—NH(C=O)CH$_2$CH$_2$NH(C=O)OCH$_2$C$_6$H$_5$) as an amorphous solid.

FAB MS (M+Li): 1291.

Part B. Hydrogenolysis

The product from Part A Example XI above (23.5 mg, 0.0183 mmol) was dissolved in 1 mL of glacial acetic acid. Next, 20.5 mg of 10% palladium on charcoal. The vessel was flushed with hydrogen gas and stirring under one atmosphere of hydrogen was continued for 3 h. The catalyst was removed by filtration, washed with methanol and the volatiles were removed by rotary evaporation under reduced pressure. The residue was dissolved in a small volume of water, frozen and lyophilized to give 17.8 mg of Compound Ex-11 as an amorphous solid.

FAB MS (M+H): 1152

EXAMPLE XII (SEQ ID NO. 23)

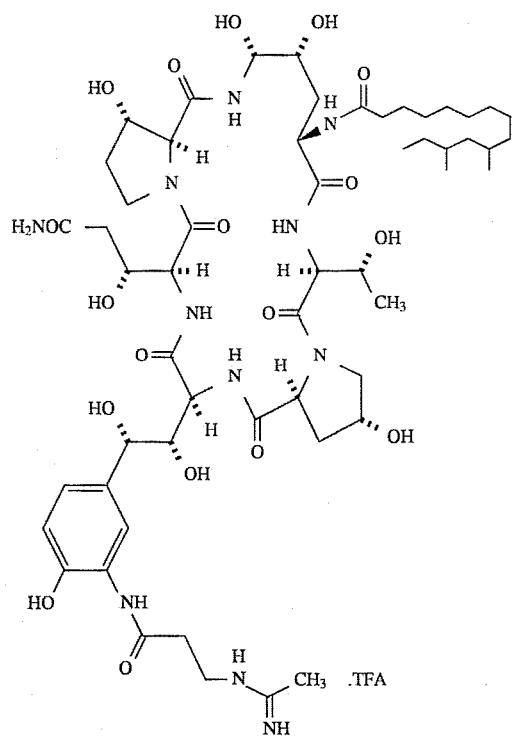

Ex-12

Compound Ex-11 (31 mg, 0.026 mmol) was dissolved in 0.4 mL of dry N,N-dimethylformamide. Ethyl acetamidate hydrochloride (4.7 mg, 0.038 mmol) was added followed by pyridine (0.0031 mL, 0.0384 mmol). The mixture was stirred at room temperature for 72 h, then, the volatiles were removed under reduced pressure. The residue was purified by preparative reverse phase HPLC (C8 ZORBAX, 50% water/50% acetonitrile/0.1% trifluoroacetic acid, λ=230, 277 nm). The appropriate fractions were combined, frozen and lyophilized to give 14.5 mg of Compound Ex-12 as an amorphous solid.

Partial $^1$H NMR (400 MHz, CD$_3$OD): δ7.76 (d, 1H), 6.97 (dd, 1H), 6.84 (d, 1H), 5.28 (d, 1H), 5.08 (m, 1H), 4.98 (d, 1H), 3.60 (m, 2H), 1.17 (d, 3 H).

FAB MS (M+Li): 1198.8.

EXAMPLE XIII (SEQ ID NO. 24)

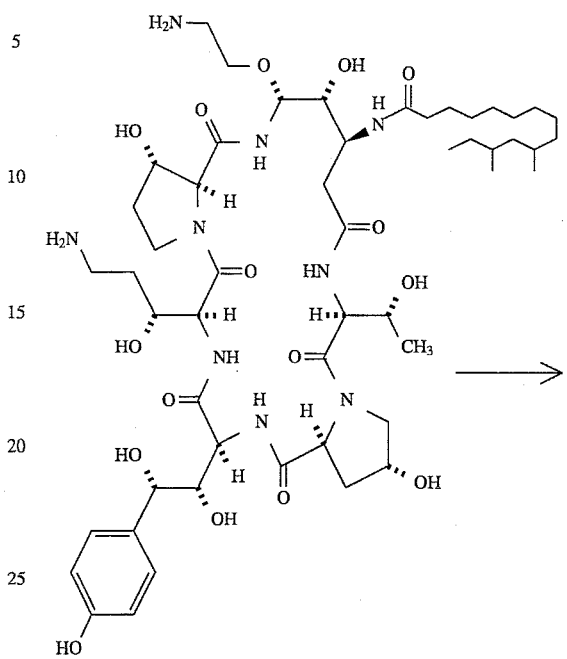

(SEQ ID NO. 25)

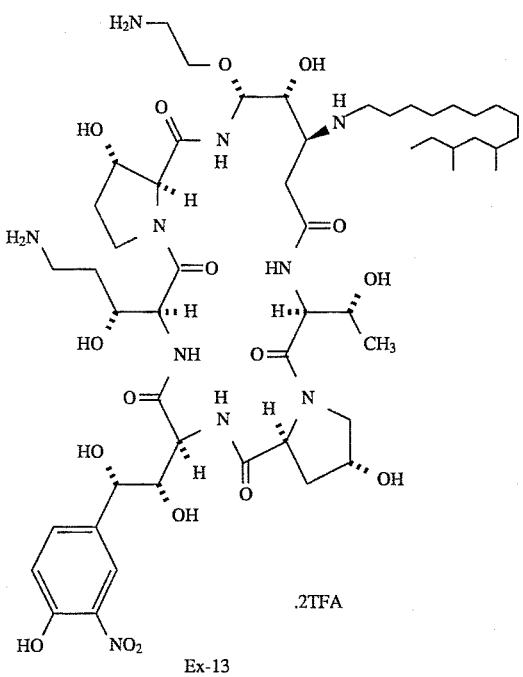

Ex-13

The starting bis-amine compound is obtained in accordance with J. Med. Chem. 37:222–225 (1994) (identified as Compound 9) and used as its dihydrochloride salt. The compound (80 mg, 0.069 mmol) was dissolved in 1.0 mL of glacial acetic acid. A 1M solution of sodium nitrite (0.288 mL, 0.288 mmol) was added and the reaction was stirred for 48 h at ambient temperature. The yellow-orange reaction mixture was diluted with approximately 5 mL of water and purified by preparative reverse phase HPLC (C18 ZORBAX, 65% water/35% acetonitrile/0.1% trifluoroacetic acid, λ=210, 277 nm). The appropriate fractions were combined, frozen and lyophilized to give 36 mg of Compound Ex-13 as a pale yellow amorphous solid.

Partial $^1$H NMR (400 MHz, CD$_3$OD): δ7.99 (d, 1H), 7.59 (dd, 1H), 7.15 (d, 1H), 5.18 (d, 1H), 4.98 (m, 1H), 3.13 (t, 2H), 3.06 (m, 2H), 1.17 (d, 3H).

ESI MS (M+H): 1139.

EXAMPLE XIV (SEQ ID NO. 26)                                      Ex-14

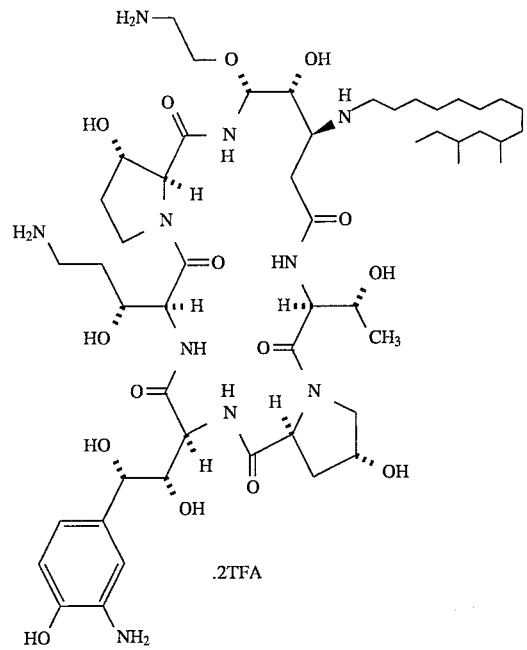

Compound Ex-13 (31.5 mg, 0.023 mmol) was dissolved in 1.0 mL of methanol. Distilled water (0.25 mL) was added. The reaction vessel was flushed with nitrogen and 10 mg of 10% Pd on charcoal was suspended in the pale yellow solution. Sodium borohydride (4.8 mg, 0.127 mmol) was added in two portions over 5 minutes. The mixture was stirred for 30 min and quenched by the addition of several drops of glacial acetic acid. The Pd-C was removed by filtration through a 0.2 micron frit and the solution was diluted with several mLs of water. The desired product was purified by preparative reverse phase HPLC (Rx C18 ZORBAX, 65% water/35% acetonitrile/0.1% TFA, λ=210, 277 nm). The appropriate fractions were combined, frozen and lyophilized to give 26 mg of Compound Ex-14 as a white amorphous solid.

Partial $^1$H NMR (400 MHz, CD$_3$OD): δ6.95 (bs, 1H), 6.78 (m, 2H), 5.17 (d, 1H), 4.98 (d, 1H), 3.13 (t, 2H), 3.07 (t, 2H), 1.17 (d, 3H).

UV spectrum (acetonitrile/water/0.1% TFA): λ$_{max}$ (nm)= 205, 222(s), 274.

ESI MS (M+H): 1109.

EXAMPLE XV (SEQ ID NO. 27)                                      Ex-15

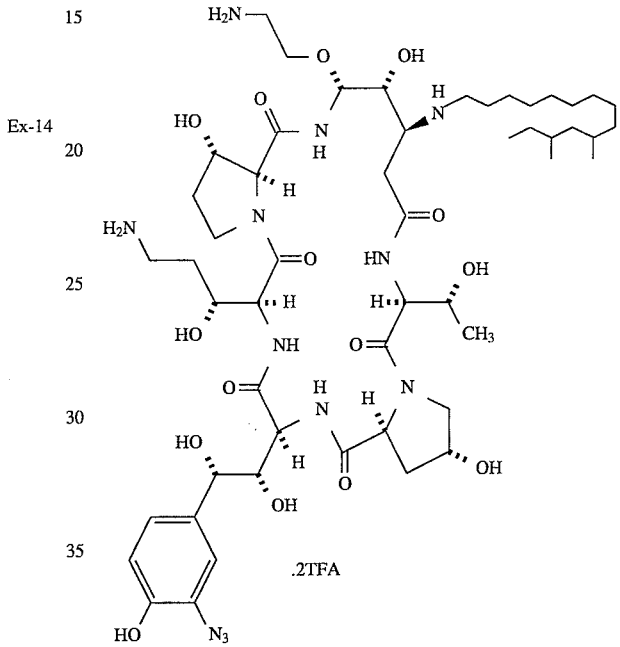

Compound Ex-14 above (23 mg, 0.017 mmol) was dissolved in 1.0 mL of glacial acetic acid. A 1N sodium nitrite solution (0.104 mL, 0.104 mmol) was added. The mixture was stirred for 10 min and a 0.5M sodium azide solution (0.412 mL, 0.206 mmol) was added. Stirring was continued at room temperature for 1 h. The mixture was purified by preparative reverse phase HPLC (Rx C18 ZORBAX, 70% water/30% acetonitrile/0.1% TFA to 60% water/acetonitrile/0.1% TFA, λ=210, 277 nm). The appropriate fractions were combined, frozen and lyophilized in the dark to give 13 mg of Compound Ex-15 as a white amorphous solid.

Partial $^1$H NMR (400 MHz, CD$_3$OD): δ6.92 (m, 2H), 6.79 (d, 1H), 5.18 (d, 1H), 4.98 (d, 1H), 3.13 (t, 2H), 3.07 (t, 2H), 1.17 (d, 3H).

UV spectrum (acetonitrile/water/0.1% TFA): λ$_{max}$ (nm)= 205, 250, 295.

ESI MS (M+H): 1135.

EXAMPLE XVI (SEQ ID NO. 28)  Ex-16

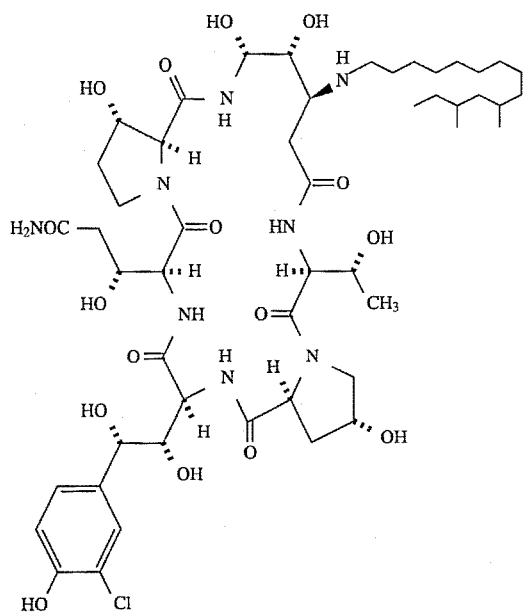

A suspension of pneumocandin B₀ (0.200 g, 0.188 mmol) in 15 mL of glacial acetic acid was heated gently to effect complete dissolution. A 5.25% aqueous w/v solution of sodium hypochlorite (0.268 mL, 0.188 mmol) was added. After stirring for min, the solution was frozen and lyophilized to give 232 mg of the crude product. Partial purification of the residue was accomplished by flash reverse phase chromatography (40% $CH_3CN$/ $H_2O$, then 50% $CH_3CN$/50% $H_2O$; LICHROPREP RP-18 [40–63 micron]). Lyophilization of the appropriate fractions gave 102 mg of material for purification by preparative reverse phase HPLC (50% $CH_3CN$/$H_2O$, C8 ZORBAX, λ=270 nm). Lyophilization of the appropriate fractions gave 62 mg of Compound Ex-16.

IR (Nujol) cm⁻¹: 3340 (br), 1720 (br), 1640 (br)

FAB MS (M+Li): 1105.

EXAMPLE XVII (SEQ ID NO. 29)  Ex-17

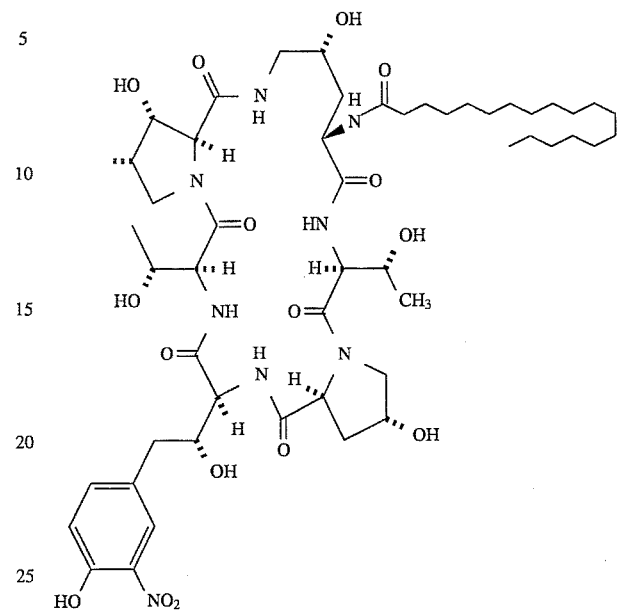

(C-5 orn, C-4 htyr)-dideoxytetrahydroechinocandin B obtained in accordance with U.S. Ser. No. 901,720 filed on Jun. 15, 1992, and in Balkovec, et al. Tetrahedron Letters, Vol. 33, pp. 4529–4532 (1992) (identified as compound 2d) (18 mg, 0.0174 mmol) and tetranitromethane (0.003 1 mL, 0.0262 mmol) were dissolved in 0.5 mL of absolute ethanol. N,N-4-Dimethylaminopyridine (approximately 3 mg) was added and the reaction mixture was stirred at room temperature for 24 h. The volatiles were removed under reduced pressure to obtain a yellow residue. The residue was purified by preparative reverse phase HPLC (30% $H_2O$/70% $CH_3CN$, C8 ZORBAX, λ=210, 277 nm) and lyophilization of the appropriate fractions gave 4.5 mg of pure nitro adduct and 3.1 mg of Compound Ex-17.

Partial ¹H NMR (400 MHz, CD₃OD): δ7.95 (d, 1H), 7.50 (dd, 1H), 7.08 (d, 1H), 4.97 (d, 1H), 4.33 (d, 1H), 2.96 (dd, 1H).

FAB MS (M+H): 1077.

EXAMPLE XVIII (SEQ ID NO. 30)                                   Ex-18

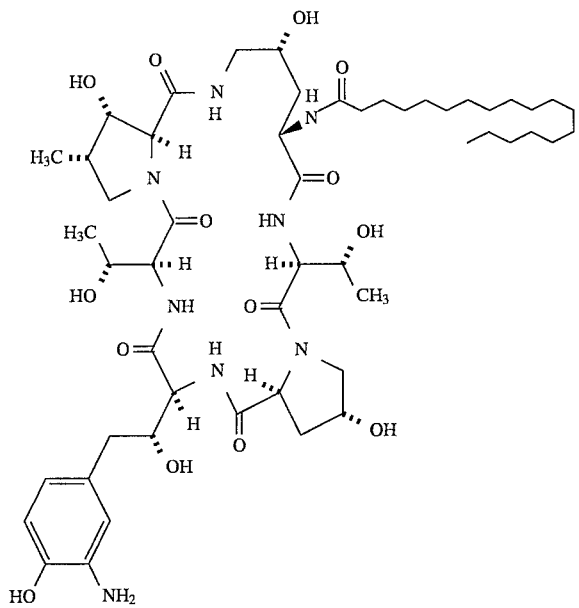

Compound Ex-17 (13 mg, 0.012 mmol) was dissolved in 1 mL of absolute ethanol. 10% palladium on charcoal (10 mg) was added and the reaction was flushed with hydrogen gas. After rapid stirring for 4 h under an atmosphere of hydrogen gas, the reaction mixture was filtered through a 0.2 micron frit. The filtrate was concentrated under reduced pressure to provide a white solid residue. Purification by reverse phase HPLC (30% H2O/70% CH3CN, C8 ZORBAX, λ= 210, 277 nm) and lyophilization of the appropriate fractions gave 8 mg of Compound Ex-18.

Partial $^1$H NMR (400 MHz, CD$_3$OD): δ6.61 (m, 2H), 6.42 (dd, 1H), 2.96 (dd, 1H).

FAB MS (M+H): 1047.

EXAMPLE XIX (SEQ ID NO. 31)                                   Ex-19

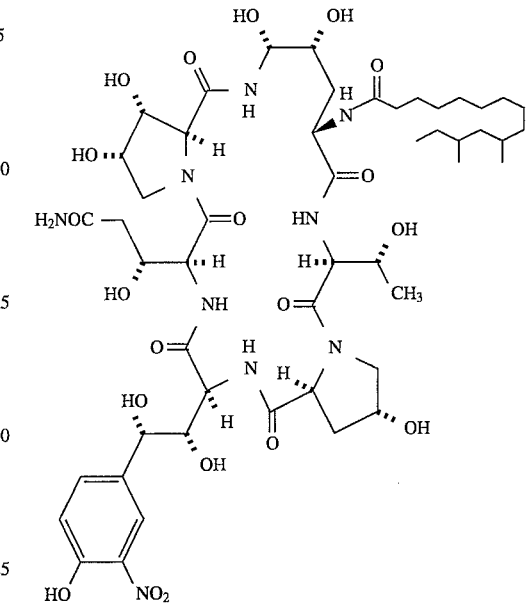

Pneumocandin D$_0$ (76 mg, 0.070 mmol) is dissolved in 1.0 mL of glacial acetic acid. A 1M solution of sodium nitrite (0.28 mL, 0.28 mmol) is added and the reaction is stirred for 48 h at ambient temperature. The reaction mixture is diluted with approximately 5 mL of water and purified by preparative reverse phase HPLC (C18 ZORBAX, 65% water/35% acetonitrile/0.1% trifluoroacetic acid, λ=210, 277 nm). The appropriate fractions are combined, frozen and lyophilized to give Compound Ex-19 with a molecular weight of 1126.3.

EXAMPLE XX (SEQ ID NO. 32)                                   Ex-20

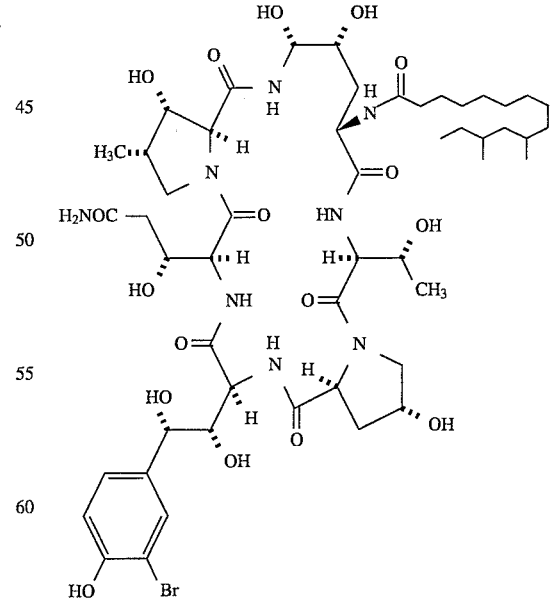

Pneumocandin $A_0$ (108 mg, 0.1 mmol) is dissolved in 10 mL glacial acetic acid. Aqueous 1M sodium hypobromite (0.1 mL, 0.1 mmol) is added dropwise at room temperature and the mixture is stirred for enough time to consume most of the pneumocandin $A_0$. The mixture is diluted with water and purified by reverse phase HPLC (C18 ZORBAX, 50% $H_2O$/50% $CH_3CN$, $\lambda$=210, 277 nm). Lyophilization of the appropriate fractions as determined by analytical HPLC give Compound Ex-20 with a molecular weight of 1158.2.

EXAMPLE XXI (SEQ ID NO. 33) (Ex-21)

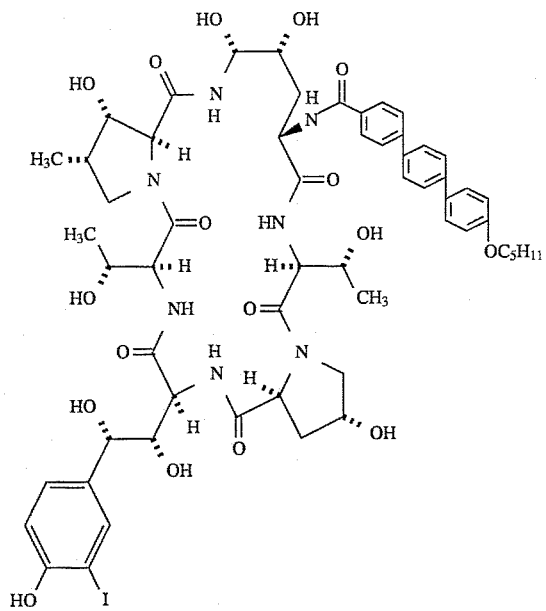

Compound PE-4 (0.1 mmol) and sodium iodide (0.1 mmol) are dissolved in 10 mL of methanol. The solution is cooled to 0° C. and aqueous sodium hypochlorite (5.25% w/v, 0.1 mmol) is added dropwise. The resultant solution is stirred at 0° C. until the majority of starting lipopeptide is consumed as determined by analytical HPLC (50% $CH_3CN$/50% $H_2O$, C18 ZORBAX, $\lambda$=210 nm). The reaction mixture is treated with a sufficient amount of 10% aqueous sodium thiosulfate to quench any excess iodinating reagent and the pH is adjusted to 7 with 2N HCl. The resulting mixture is diluted with water, filtered, and purified by reverse phase HPLC (C18 ZORBAX, 50% $H_2O$ / 50% $CH_3CN$, $\lambda$=210 nm). Lyophilization of the appropriate fractions as determined by analytical HPLC give Compound Ex-21 with a molecular weight of 1266.16.

EXAMPLE XXII (SEQ ID NO. 34) Ex-22

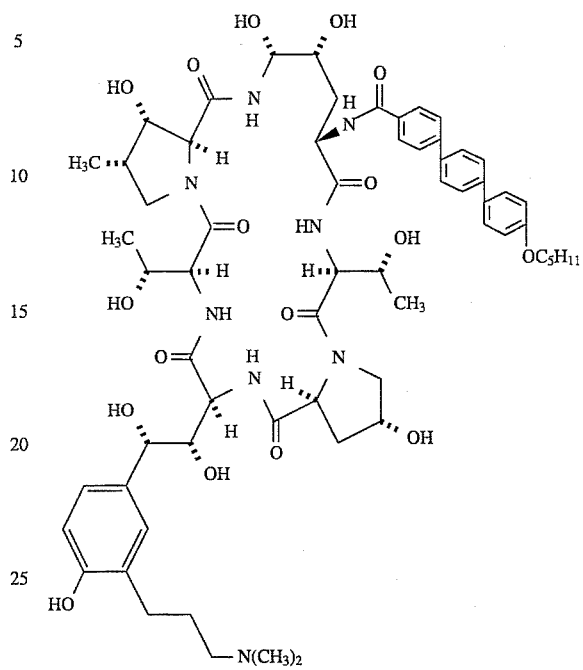

Part A. Palladium Coupling

To a solution of Compound Ex-21 (0.1 mmol) in 1-methyl- 2-pyrrolidinone (10 mL) is added tetrakis(triphenylphosphine)palladium( 0) (0.0 10 mmol) followed by tetra(3-butenyl)tin (0.15 mmol). Lithium chloride (0,017 mmol) is then added and the mixture is stirred at 60° C. until analytical HPLC (C18 ZORBAX, 35% $H_2O$/65% $CH_3CN$, $\lambda$=210 nm) shows conversion of starting material to a product. The reaction mixture is diluted with water, filtered and injected onto a preparative HPLC column (C18 ZORBAX, 50% $H_2O$/50% $CH_3CN$, $\lambda$=210 nm). The appropriate fractions as determined by analytical HPLC are combined and lyophilized to give the homoallyl adduct ($R^8$=—$CH_2CH_2CH$=$CH_2$) of molecular weight 1194.36.

Part B. Ozonolysis

A solution of the product from part A above, (0.1 mmol) in 5 mL of methanol is added to a saturated solution of ozone in dichloromethane at –78° C. (2.5 mL, ~0.04M, 0.1 mmol). The resultant solution is stirred at –78° C. for 15 minutes and is then allowed to warm to room temperature. Methyl sulfide (1 mL, 13 mmol) is added and the reaction mixture is stirred overnight. The solution is diluted with water and purified by preparative HPLC (C18 ZORBAX, 45% $CH_3CN$/55% $H_2O$, $\lambda$=210 nm). Lyophilization of the appropriate fractions as determined by analytical HPLC (35% $H_2O$/65% $CH_3CN$, C18 ZORBAX, $\lambda$=210 nm) gives the aldehyde ($R^8$=—$CH_2CH_2CH$=O) with a molecular weight of 1196.33.

Part C. Reductive Amination

To a solution of the product from part B above (0.01 mmol) in 0.5 mL of methanol is added dimethylammonium acetate (0.1 mmol) and sodium cyanoborohydride (0.016 mmol). The resultant mixture is stirred at room temperature overnight. The reaction mixture is then diluted to about 5 mL with water, filtered and injected onto a preparative HPLC column (Rx C18 ZORBAX, 50% CH₃CN/50% H₂O/ 0.1% TFA, λ=210 nm). Lyophilization of the appropriate fractions gives Compound Ex-22 with a molecular weight of 1139.44.

EXAMPLE XXIII (SEQ ID NO. 35)                                    Ex-23

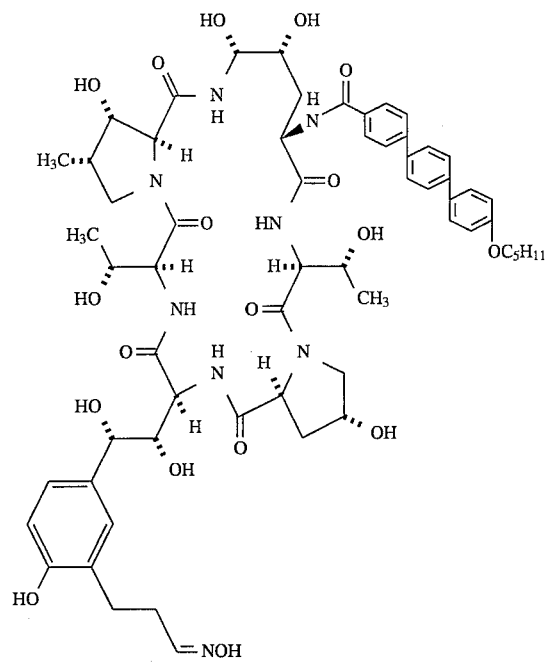

To a solution of the product from part B, example XXII, above (0.05 mmol) in 1.0 mL of pyridine is added hydroxylamine hydrochloride (0.1 mmol). The resultant solution is stirred at room temperature for 2 hours. The reaction mixture is concentrated by rotary evaporation, diluted with 1:1 CH₃CN/H₂O, filtered, and purified by preparative HPLC (45% H₂O/55% CH₃CN, C18 ZORBAX, λ=210 nm). Lyophilization of the appropriate fractions as determined by analytical HPLC (40% H₂O/ 60% CH₃CN, C18 ZORBAX, λ=210 nm) gives Compound Ex-23 with a molecular weight of 1211.34.

EXAMPLES XXIV–XXVIII

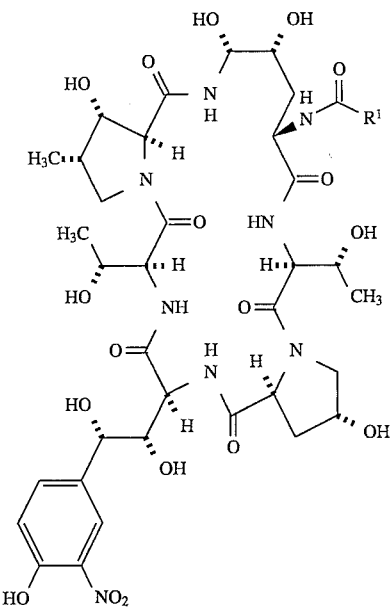

In a manner similar to Example VII above, the following nitro compounds represented by the above structure are prepared, varying the nature of the group $R^I$. The starting hexapeptides may be prepared in accordance with the general procedure for the N-acylation of the A30912A cyclohexapeptide nucleus found in EP 0561639-A1 published on Sep. 22, 1993, modified to include an appropriate activated ester in place of a 2, 4, 5-trichlorophenyl ester. Appropriate activated esters for acylation of the nucleus are precisely described in EP 048601 1-A2 published on May 20, 1992.

| Example | $R^1$ | Sequence ID |
|---|---|---|
| XXIV | —C₆H₄—C₆H₄—OC₈H₁₇ | SEQ ID NO. 36 |
| XXV | —C₆H₄—O(CH₂)₂O(CH₂)₇CH₃ | SEQ ID NO. 37 |
| XXVI | (farnesyl chain) | SEQ ID NO. 38 |
| XXVII | (anthracenyl) | SEQ ID NO. 39 |
| XXVIII | (naphthyl)—OC₈H₁₇ | SEQ ID NO. 40 |

What is claimed is:

1. A compound represented by the formula I:

(SEQ ID NO. 1)

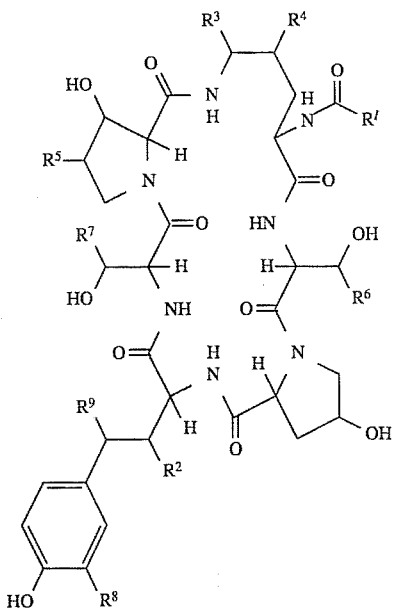

I or a pharmaceutically acceptable salt or hydrate thereof wherein:

$R^I$ represents $C_9$ to $C_{19}$ alkyl, $C_9$ to $C_{19}$ alkenyl, aryl selected from the group consisting of: phenyl, biphenyl, naphthyl and terphenyl; or a $C_1$ to $C_{12}$ alkyl, alkylamino, dialkylamino or alkoxyaryl group;

$R^9$, $R^2$ and $R^4$ independently represent H or —OH;

$R^3$ represents H, —OH, —O(CH$_2$)$_n$NR$^V$R$^{VI}$, where $R^V$ and $R^{VI}$ independently represent H or $C_{1-4}$ alkyl, or —O(CH$_2$)$_n$NR$^V$R$^{VI}$R$^{VII+}$Y$^-$, wherein $R^V$ and $R^{VI}$ are as defined above, $R^{VII}$ represents H or $C_{1-4}$ alkyl, n is an integer of from 2–6 inclusive, and Y represents a counterion;

$R^5$ represents H, —CH$_3$ or —OH;

$R^6$ represents H or —CH$_3$;

$R^7$ represents H, —CH$_3$, —CH$_2$C(=O)NH$_2$, —(CH$_2$)$_2$NR$^V$R$^{VI}$ or —(CH$_2$)$_2$NR$^V$R$^{VI}$R$^{VII+}$Y$^-$ with n, $R^V$, $R^{VI}$ $R^{VII}$ and Y as defined above;

and $R^8$ represents —Cl, —Br, —I, —NO$_2$, —N$_3$, —(CH$_2$)$_{0-4}$NR$^V$R$^{VI}$ wherein $R^V$ and $R^{VI}$ are as previously defined, —(CH$_2$)$_{0-3}$CH(=NOH), —NHC(=O)(CH$_2$)$_{1-6}$NH$_2$ or —NHC(=O)(CH$_2$)$_{1-6}$NHC(=NH)(CH$_2$)$_{0-3}$H.

2. A compound in accordance with claim 1 represented by the structural formula:

(SEQ ID NO. 3)

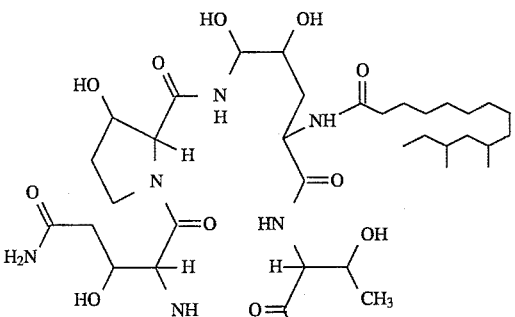
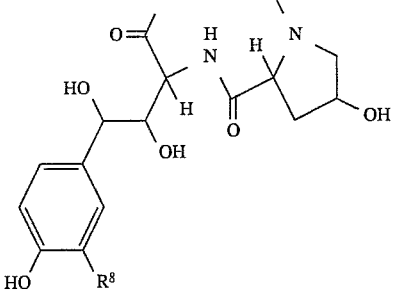

I-a wherein $R^8$ represents a member selected from the group consisting of —Cl, —I, —NO$_2$, —NH$_2$, —N$_3$— NHC(O)CH$_2$NH$_2$, —NHC(O)CH$_2$CH$_2$NH$_2$ and —NHC(O)CH$_2$CH$_2$N(C=NH)CH$_3$.

3. A compound in accordance with claim I represented by the structural formula:

(SEQ ID NO. 4)    I-b

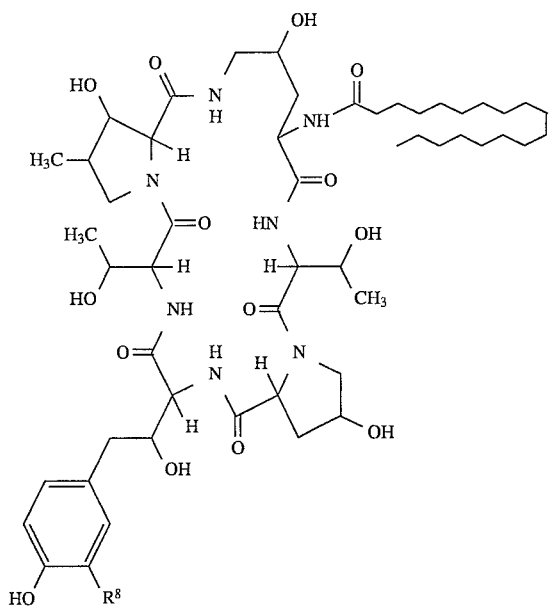

wherein $R^8$ represents $NH_2$ or $NO_2$.

4. A compound in accordance with claim 1 represented by the structural formula:

(SEQ ID NO. 5)    I-c

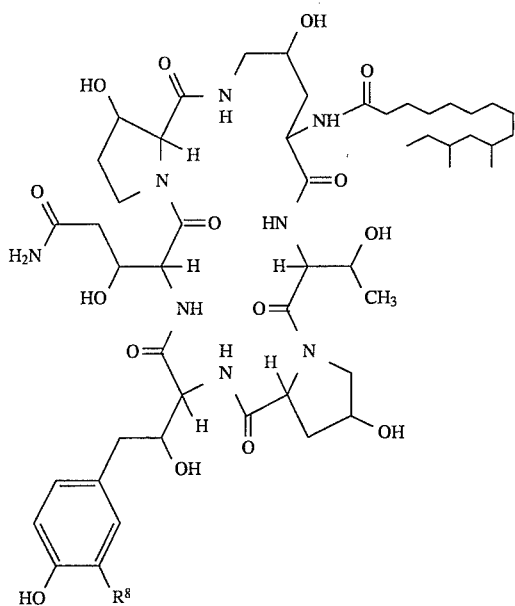

wherein $R^8$ represents I, $NO_2$, $NH_2$, $-N_3$, $-CH_2CH(=NOH)$, $-CH_2CH_2NH_2$.

5. A compound in accordance with claim 1 represented by the structural formula:

(SEQ ID NO. 6)    I-d

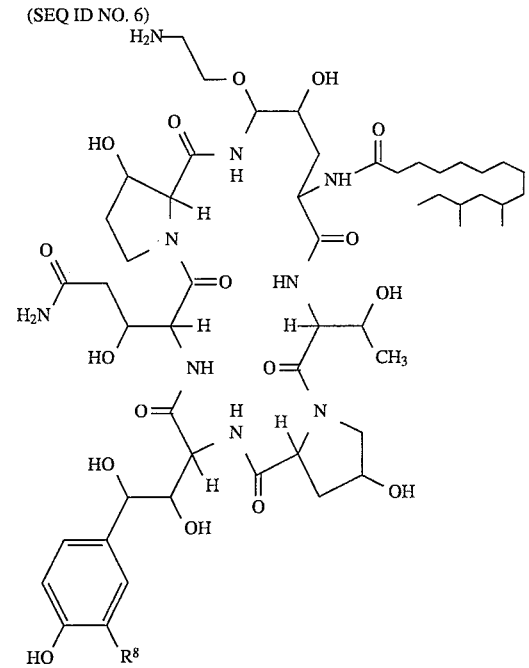

wherein $R^8$ is represented by $NH(C=O)CH_2NH_2$.

6. A compound in accordance with claim I represented by the structural formula:

(SEQ ID NO. 7)    I-e

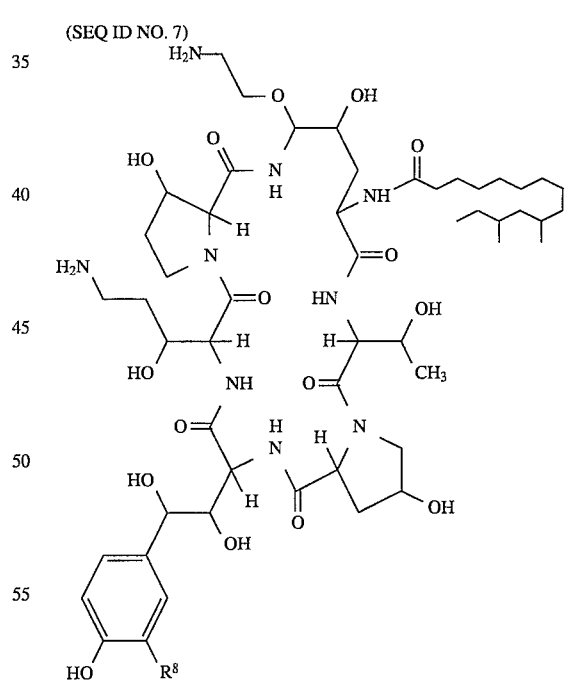

wherein $R^8$ represents $-NO_2$, $-NH_2$ or $-N_3$.

7. A compound represented by one of the following structural formulas:

(SEQ ID NO. 12) Ex-1

(SEQ ID NO. 13) Ex-2

(SEQ ID NO. 14) Ex-3

(SEQ ID NO. 15) Ex-4

-continued
(SEQ ID NO. 16) Ex-5
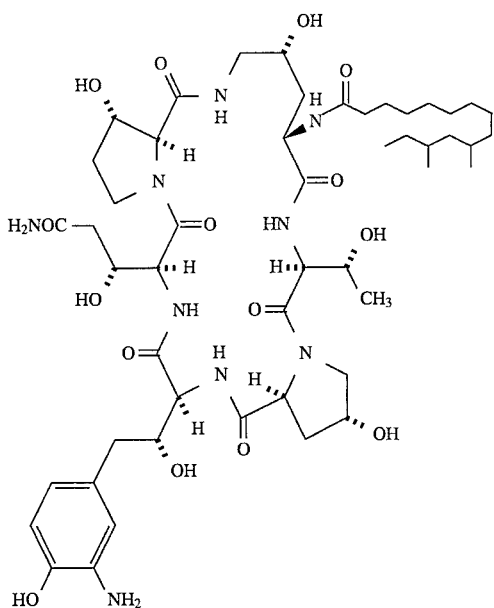
(SEQ ID NO. 17) Ex-6
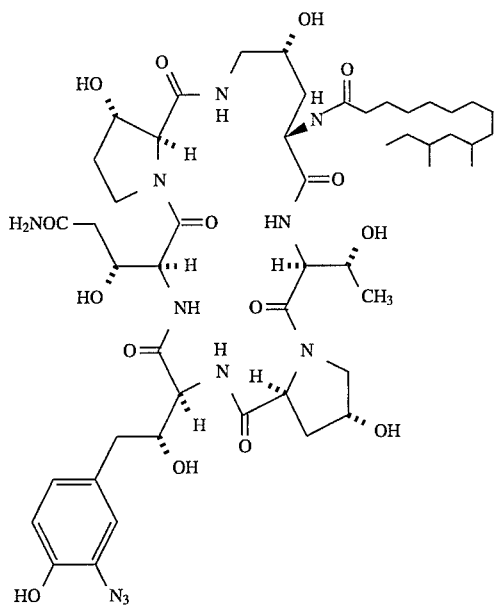
-continued
(SEQ ID NO. 18) Ex-7
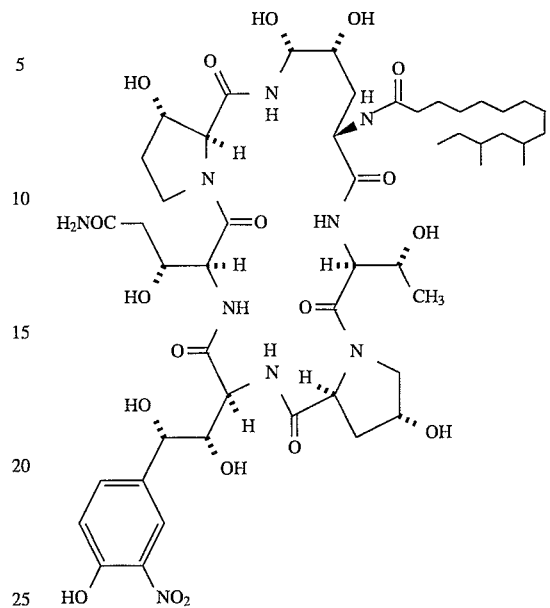
(SEQ ID NO. 19) Ex-8
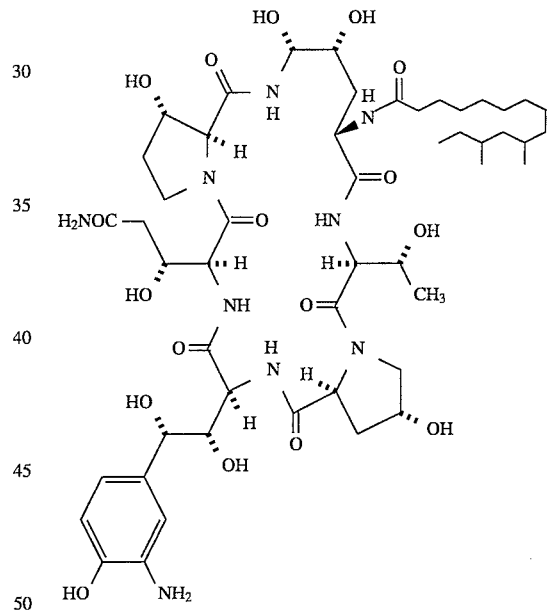

(SEQ ID NO. 20) Ex-9
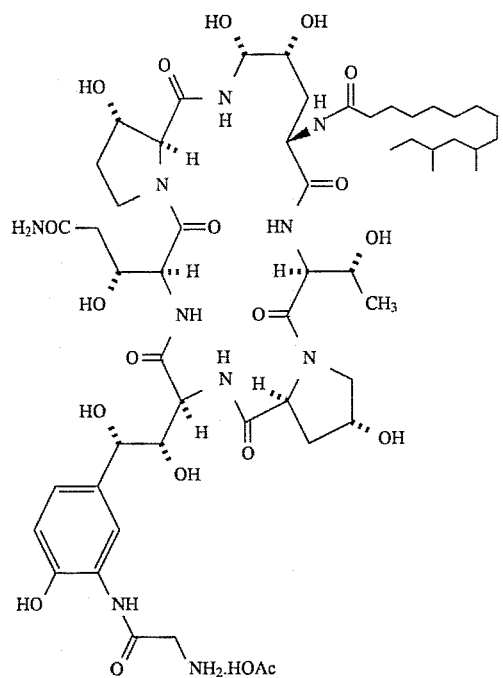
(SEQ ID NO. 21) Ex-10
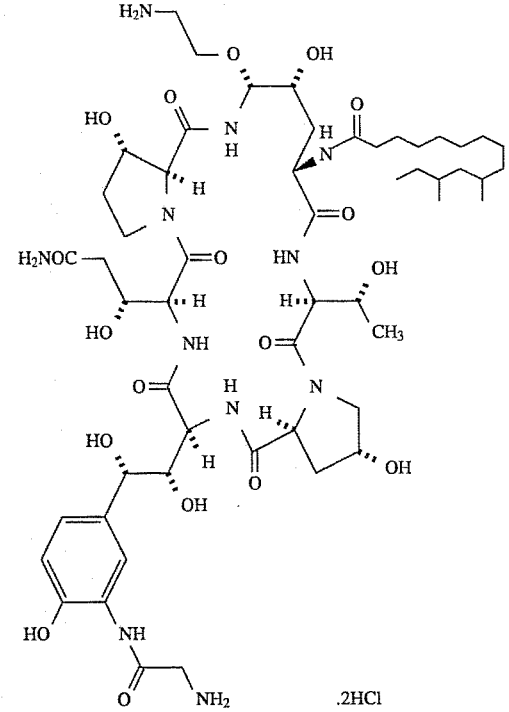
(SEQ ID NO. 22) Ex-11
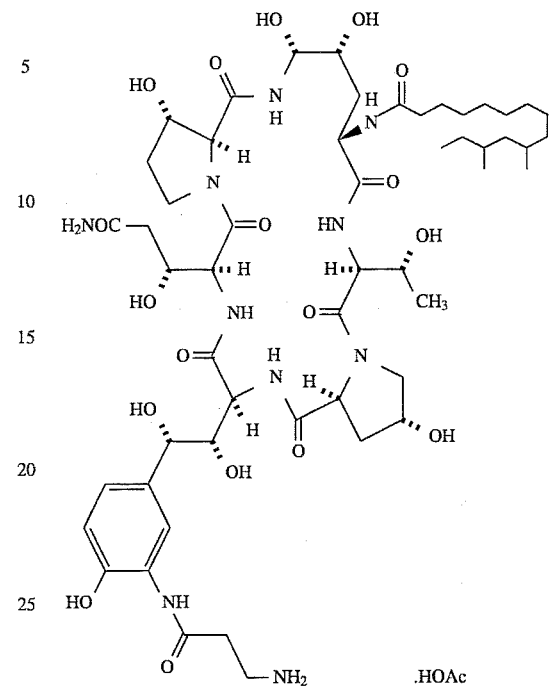
(SEQ ID NO. 23) Ex-12
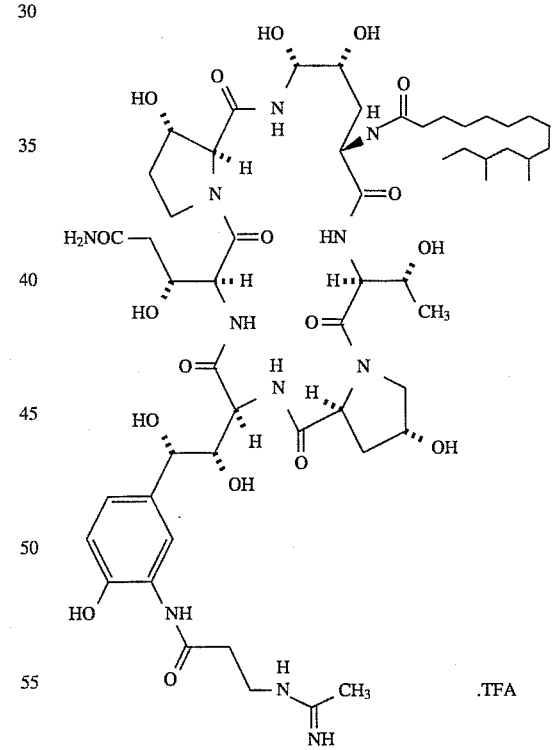

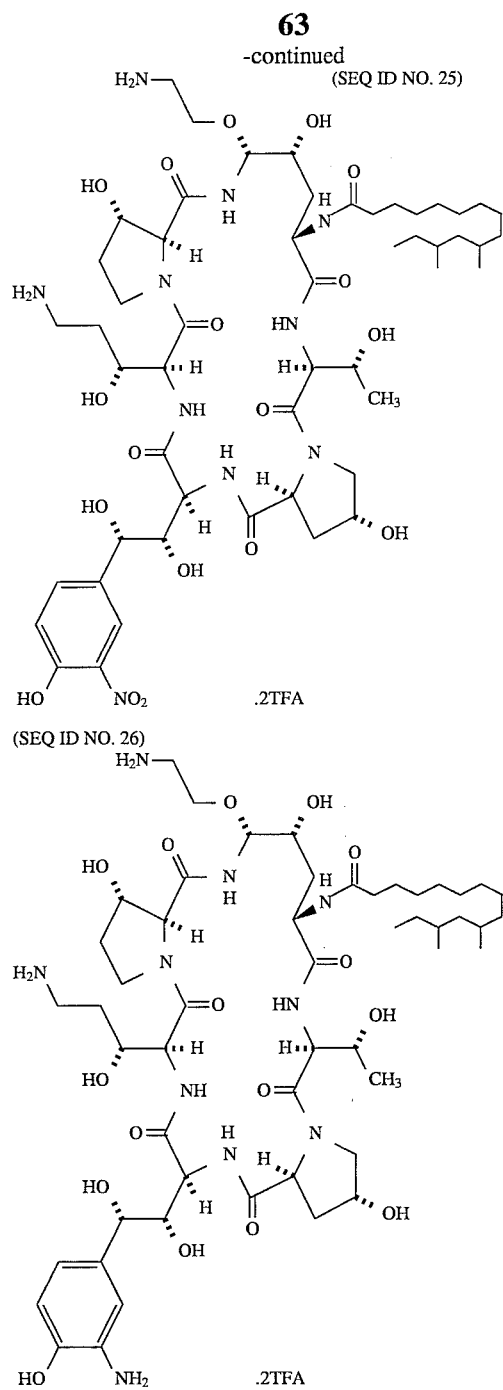

-continued
(SEQ ID NO. 29) Ex-17
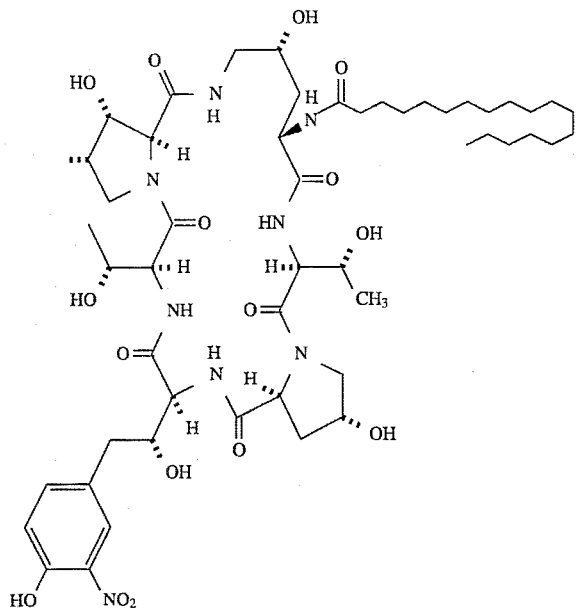
(SEQ ID NO. 30) Ex-18
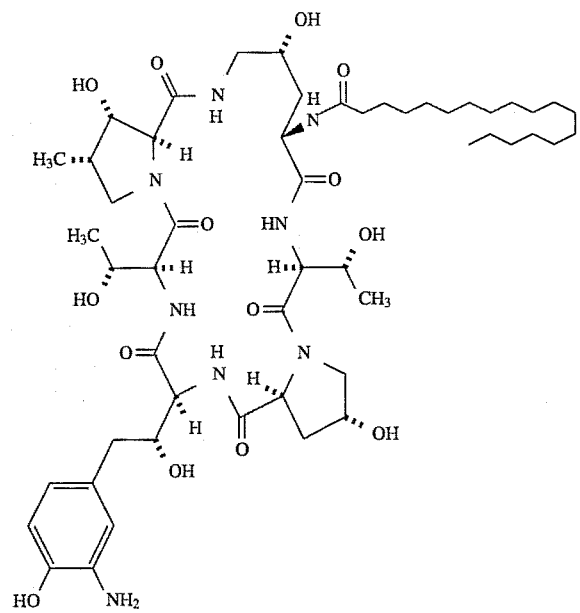
(SEQ ID NO. 31) Ex-19
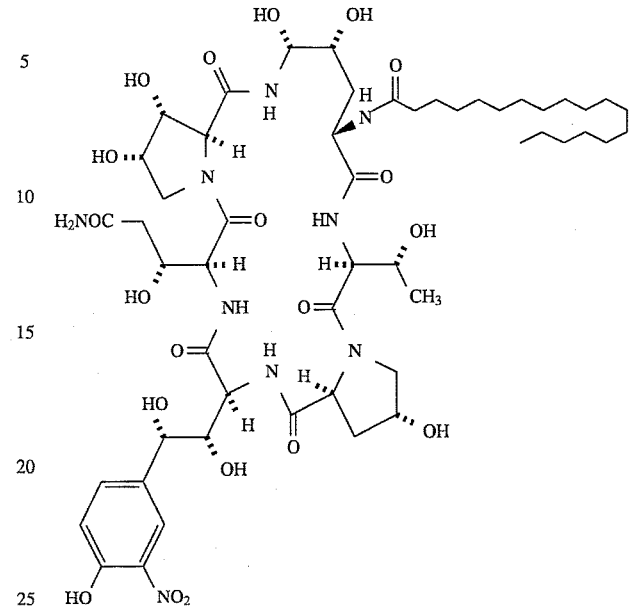
(SEQ ID NO. 32) Ex-20
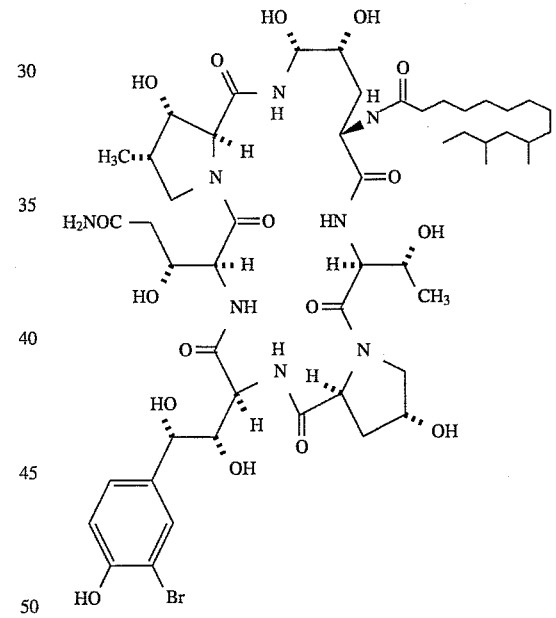

(SEQ ID NO. 33) (Ex-21)
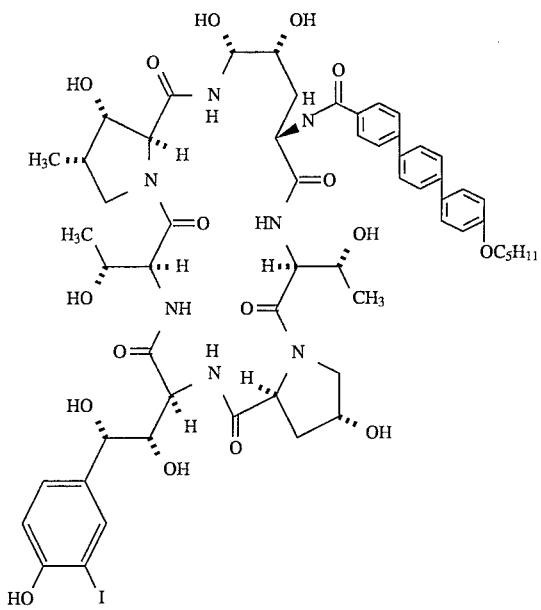
(SEQ ID NO. 34) (Ex-22)
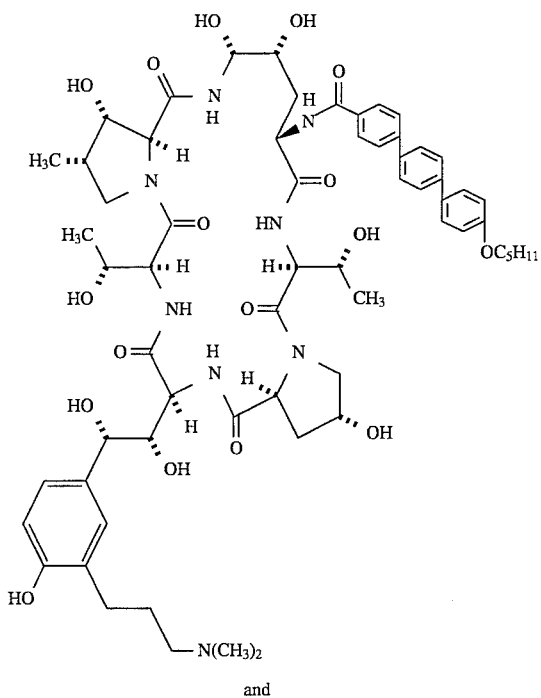
and
(SEQ ID NO. 35) (Ex-23)
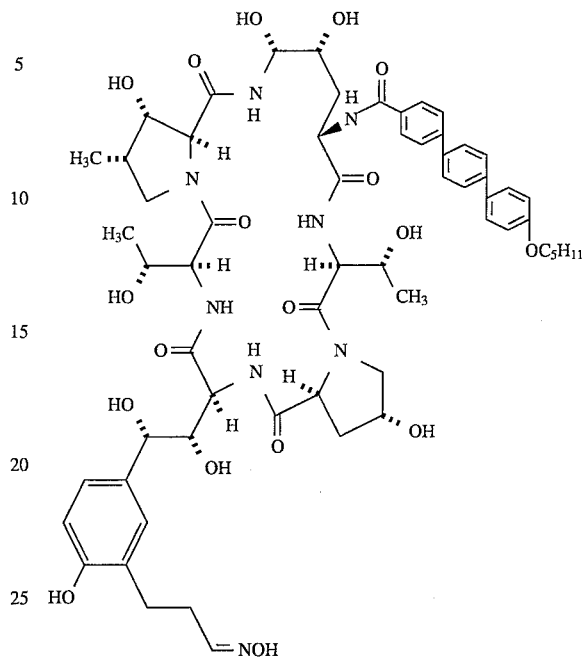
8. A compound represented by the formula:
(SEQ ID NOS. 36–41)
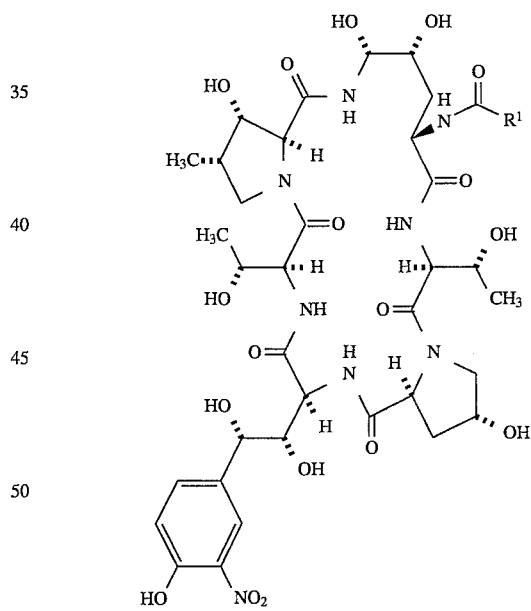
wherein the value of $R^1$ is selected from the group consisting of:
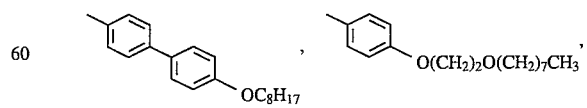
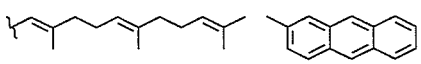
and -continued

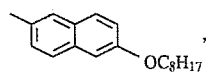

9. A pharmaceutical composition comprised of a compound in accordance with claim 1 in combination with a pharmaceutically acceptable carrier.

10. A method of treating a fungal infection in a mammalian patient in need of such treatment comprising administering a compound in accordance with claim 1 to said patient in an amount effective to treat said fungal infection.

11. A method of treating a Pneumocystis infection in a mammalian patient in need of such treatment comprising administering a compound in accordance with claim 1 to said patient in an amount effective to treat said Pneumocystis infection.

12. A method of preventing a Pneumocystis infection in an immunocompromised mammalian patient in need of such treatment comprising administering a compound in accordance with claim 1 to said patient in an amount effective to prevent said Pneumocystis infection.

* * * * *

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Xaa  Xaa  Xaa  Xaa  Xaa  Xaa
1                   5
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:2:

```
Xaa  Thr  Xaa  Xaa  Thr  Xaa
1                   5
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:3:

```
Xaa  Thr  Xaa  Xaa  Xaa  Xaa
1                   5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:4:

```
Xaa  Thr  Xaa  Xaa  Thr  Xaa
1                   5
```

( 2 ) INFORMATION FOR SEQ ID NO:5:

( i ) SEQUENCE CHARACTERISTICS:
        ( A ) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:5:

Xaa Thr Xaa Xaa Xaa Xaa
1               5

(2) INFORMATION FOR SEQ ID NO:6:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:6:

Xaa Thr Xaa Xaa Xaa Xaa
1               5

(2) INFORMATION FOR SEQ ID NO:7:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:7:

Xaa Thr Xaa Xaa Xaa Xaa
1               5

(2) INFORMATION FOR SEQ ID NO:8:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:8:

Xaa Thr Xaa Xaa Xaa Xaa
1               5

(2) INFORMATION FOR SEQ ID NO:9:

(i) SEQUENCE CHARACTERISTICS:
    (A) LENGTH: 6 amino acids
    (B) TYPE: amino acid
    (C) STRANDEDNESS: unknown
    (D) TOPOLOGY: circular (ii) MOLECULE TYPE: peptide (xi) SEQUENCE DESCRIPTION: SEQ ID NO:9:

Xaa Thr Xaa Xaa Xaa Xaa
1               5

(2) INFORMATION FOR SEQ ID NO:10:

(i) SEQUENCE CHARACTERISTICS:
    (A) LENGTH: 6 amino acids ( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:10:

Xaa Thr Xaa Xaa Thr Xaa
1               5

( 2 ) INFORMATION FOR SEQ ID NO:11:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:11:

Xaa Thr Xaa Xaa Thr Xaa
1               5

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:12:

Xaa Thr Xaa Xaa Xaa Xaa
1               5

( 2 ) INFORMATION FOR SEQ ID NO:13:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:13:

Xaa Thr Xaa Xaa Xaa Xaa
1               5

( 2 ) INFORMATION FOR SEQ ID NO:14:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:14:

Xaa Thr Xaa Xaa Xaa Xaa
1               5

( 2 ) INFORMATION FOR SEQ ID NO:15:

( i ) SEQUENCE CHARACTERISTICS:
( A ) LENGTH: 6 amino acids ( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:15:

Xaa Thr Xaa Xaa Xaa Xaa
1               5

( 2 ) INFORMATION FOR SEQ ID NO:16:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:16:

Xaa Thr Xaa Xaa Xaa Xaa
1               5

( 2 ) INFORMATION FOR SEQ ID NO:17:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:17:

Xaa Thr Xaa Xaa Xaa Xaa
1               5

( 2 ) INFORMATION FOR SEQ ID NO:18:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:18:

Xaa Thr Xaa Xaa Xaa Xaa
1               5

( 2 ) INFORMATION FOR SEQ ID NO:19:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:19:

Xaa Thr Xaa Xaa Xaa Xaa
1               5

( 2 ) INFORMATION FOR SEQ ID NO:20:

( i ) SEQUENCE CHARACTERISTICS:
( A ) LENGTH: 6 amino acids ( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:20:

Xaa Thr Xaa Xaa Xaa Xaa
1             5

( 2 ) INFORMATION FOR SEQ ID NO:21:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:21:

Xaa Thr Xaa Xaa Xaa Xaa
1             5

( 2 ) INFORMATION FOR SEQ ID NO:22:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:22:

Xaa Thr Xaa Xaa Xaa Xaa
1             5

( 2 ) INFORMATION FOR SEQ ID NO:23:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:23:

Xaa Thr Xaa Xaa Xaa Xaa
1             5

( 2 ) INFORMATION FOR SEQ ID NO:24:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:24:

Xaa Thr Xaa Xaa Xaa Xaa
1             5

( 2 ) INFORMATION FOR SEQ ID NO:25:

( i ) SEQUENCE CHARACTERISTICS:
( A ) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:25:

Xaa Thr Xaa Xaa Xaa Xaa
1               5

(2) INFORMATION FOR SEQ ID NO:26:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:26:

Xaa Thr Xaa Xaa Xaa Xaa
1               5

(2) INFORMATION FOR SEQ ID NO:27:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:27:

Xaa Thr Xaa Xaa Xaa Xaa
1               5

(2) INFORMATION FOR SEQ ID NO:28:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:28:

Xaa Thr Xaa Xaa Xaa Xaa
1               5

(2) INFORMATION FOR SEQ ID NO:29:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:29:

Xaa Thr Xaa Xaa Thr Xaa
1               5

(2) INFORMATION FOR SEQ ID NO:30:

(i) SEQUENCE CHARACTERISTICS:
(A) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:30:

```
Xaa  Thr  Xaa  Xaa  Thr  Xaa
1                 5
```

(2) INFORMATION FOR SEQ ID NO:31:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:31:

```
Xaa  Thr  Xaa  Xaa  Xaa  Xaa
1                 5
```

(2) INFORMATION FOR SEQ ID NO:32:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:32:

```
Xaa  Thr  Xaa  Xaa  Xaa  Xaa
1                 5
```

(2) INFORMATION FOR SEQ ID NO:33:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:33:

```
Xaa  Thr  Xaa  Xaa  Thr  Xaa
1                 5
```

(2) INFORMATION FOR SEQ ID NO:34:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:34:

```
Xaa  Thr  Xaa  Xaa  Thr  Xaa
1                 5
```

(2) INFORMATION FOR SEQ ID NO:35:

(i) SEQUENCE CHARACTERISTICS:
(A) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:35:

Xaa  Thr  Xaa  Xaa  Thr  Xaa
1                  5

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS: unknown
        (D) TOPOLOGY: circular (ii) MOLECULE TYPE: peptide (xi) SEQUENCE DESCRIPTION: SEQ ID NO:36:

Xaa  Thr  Xaa  Xaa  Thr  Xaa
1                  5

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: unknown
        (D) TOPOLOGY: circular (ii) MOLECULE TYPE: peptide (xi) SEQUENCE DESCRIPTION: SEQ ID NO:37:

Xaa  Thr  Xaa  Xaa  Thr  Xaa
1                  5

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS: unknown
        (D) TOPOLOGY: circular (ii) MOLECULE TYPE: peptide (xi) SEQUENCE DESCRIPTION: SEQ ID NO:38:

Xaa  Thr  Xaa  Xaa  Thr  Xaa
1                  5

(2) INFORMATION FOR SEQ ID NO:39:

(i) SEQUENCE CHARACTERISTICS:
        (A) LENGTH: 6 amino acids
        (B) TYPE: amino acid
        (C) STRANDEDNESS: unknown
        (D) TOPOLOGY: circular (ii) MOLECULE TYPE: peptide (xi) SEQUENCE DESCRIPTION: SEQ ID NO:39:

Xaa  Thr  Xaa  Xaa  Thr  Xaa
1                  5

(2) INFORMATION FOR SEQ ID NO:40:

(i) SEQUENCE CHARACTERISTICS:
        (A) LENGTH: 6 amino acids (B) TYPE: amino acid
(C) STRANDEDNESS: unknown
(D) TOPOLOGY: circular (ii) MOLECULE TYPE: peptide (xi) SEQUENCE DESCRIPTION: SEQ ID NO:40:

Xaa Thr Xaa Xaa Thr Xaa
1               5